US008807412B2

(12) United States Patent
Thomas et al.

(10) Patent No.: US 8,807,412 B2
(45) Date of Patent: Aug. 19, 2014

(54) MEDICAL DEVICE ACCESSORY CARRIER

(75) Inventors: Ralph Thomas, Livermore, CA (US);
Thomas Orduna, Oakley, CA (US);
Maximillian Gubbins, Surrey (GB);
Edward Geiselhart, Chicago, IL (US);
David C. Brown, Chicago, IL (US)

(73) Assignee: Thoratec Corporation, Pleasanton, CA (US)

( * ) Notice: Subject to any disclaimer, the term of this patent is extended or adjusted under 35 U.S.C. 154(b) by 283 days.

(21) Appl. No.: 12/620,306

(22) Filed: Nov. 17, 2009

(65) Prior Publication Data

US 2010/0122995 A1    May 20, 2010

Related U.S. Application Data

(60) Provisional application No. 61/115,796, filed on Nov. 18, 2008.

(51) Int. Cl.
| | | |
|---|---|---|
| A45C 1/04 | (2006.01) | |
| A45F 3/00 | (2006.01) | |
| F41C 33/02 | (2006.01) | |
| F42B 39/02 | (2006.01) | |
| A45F 3/10 | (2006.01) | |
| A45F 5/00 | (2006.01) | |
| A61M 5/32 | (2006.01) | |
| A61F 5/44 | (2006.01) | |
| A61B 19/00 | (2006.01) | |

(52) U.S. Cl.
USPC ........... 224/660; 224/663; 224/664; 224/665; 224/666; 224/672; 224/677; 224/684; 224/269; 224/930; 604/179; 604/355; 604/356; 604/388

(58) Field of Classification Search
USPC ......... 224/660, 663, 664, 665, 666, 672, 677, 224/684, 269, 930; 604/179, 355, 356, 388
See application file for complete search history.

(56) References Cited

U.S. PATENT DOCUMENTS 44,993 A * 11/1864 Woods .......................... 224/583
2,625,192 A * 1/1953 Kinskie ......................... 224/665
(Continued)

FOREIGN PATENT DOCUMENTS

| JP | 61502030 | 9/1986 |
|---|---|---|
| JP | 05-329121 | 12/1993 |

(Continued)

OTHER PUBLICATIONS

International Search Report and Written Opinion from Corresponding PCT Application No. PCT/US2009/064835 dated Jun. 24, 2010, (11 pgs).

(Continued)

*Primary Examiner* — Brian D Nash
*Assistant Examiner* — Derek Battisti
(74) *Attorney, Agent, or Firm* — Kilpatrick Townsend and Stockton LLP

(57) ABSTRACT

A carrier system for carrying medical device accessories includes a first battery pouch to enclose at least a portion of a first battery and a garment to be worn about a torso. The garment including a plurality of accessory connection features adapted to allow for adjustable attachment of at least the first battery pouch and for adjustable attachment of a medical device controller that is electrically connected to a medical device.

23 Claims, 18 Drawing Sheets

(56) References Cited

U.S. PATENT DOCUMENTS

| | | | | |
|---|---|---|---|---|
| 3,919,615 | A * | 11/1975 | Niecke | 320/112 |
| 4,214,688 | A * | 7/1980 | Griffin, Jr. | 224/197 |
| 4,384,372 | A * | 5/1983 | Rector | 2/300 |
| 4,411,267 | A | 10/1983 | Heyman | |
| 4,600,134 | A * | 7/1986 | Colby | 224/260 |
| 4,793,486 | A | 12/1988 | Konopka et al. | |
| 5,059,182 | A * | 10/1991 | Laing | 604/142 |
| 5,152,443 | A | 10/1992 | Hagan | |
| 5,211,321 | A * | 5/1993 | Rodriguez | 224/604 |
| 5,259,093 | A * | 11/1993 | D'Annunzio | 24/3.9 |
| 5,263,618 | A * | 11/1993 | Talavera | 224/148.5 |
| 5,284,470 | A | 2/1994 | Beltz | |
| 5,358,159 | A * | 10/1994 | Lundie, Jr. | 224/624 |
| 5,392,973 | A | 2/1995 | Benson | |
| D358,475 | S | 5/1995 | Choksi et al. | |
| 5,524,802 | A | 6/1996 | Benson et al. | |
| 5,613,935 | A | 3/1997 | Jarvik | |
| 5,653,367 | A * | 8/1997 | Abramson | 224/581 |
| 5,727,720 | A * | 3/1998 | Thatcher | 224/664 |
| 5,741,306 | A | 4/1998 | Glegyak et al. | |
| 5,746,365 | A * | 5/1998 | Scott | 224/676 |
| 5,775,558 | A * | 7/1998 | Montalbano | 224/627 |
| 5,816,460 | A * | 10/1998 | Cook | 224/260 |
| 5,915,609 | A | 6/1999 | Diakoulas | |
| 6,015,399 | A | 1/2000 | Mracna et al. | |
| 6,289,896 | B1 | 9/2001 | Hart | |
| 6,543,661 | B1 * | 4/2003 | Lazur | 224/604 |
| 6,561,814 | B2 | 5/2003 | Tilbury et al. | |
| 6,568,575 | B1 * | 5/2003 | Bartholomew | 224/583 |
| 6,681,404 | B1 | 1/2004 | Adlard et al. | |
| 6,698,631 | B1 * | 3/2004 | Haskins | 224/148.4 |
| 6,752,299 | B2 | 6/2004 | Shetler et al. | |
| 6,923,302 | B2 * | 8/2005 | Godshaw et al. | 190/109 |
| 6,923,357 | B2 * | 8/2005 | Smith | 224/605 |
| 7,282,044 | B2 * | 10/2007 | Hudson et al. | 604/174 |
| 7,370,781 | B2 * | 5/2008 | Gambrill | 224/647 |
| 7,770,770 | B2 * | 8/2010 | Murdoch et al. | 224/672 |
| 8,302,830 | B1 * | 11/2012 | Jensen et al. | 224/625 |
| 2002/0170933 | A1 * | 11/2002 | Martin | 224/197 |
| 2006/0211937 | A1 | 9/2006 | Eldridge | |
| 2008/0027341 | A1 | 1/2008 | Sackner et al. | |
| 2009/0039120 | A1 * | 2/2009 | Murdoch et al. | 224/195 |

FOREIGN PATENT DOCUMENTS

| | | |
|---|---|---|
| JP | 2000-051373 | 2/2000 |
| JP | 2005-342436 | 12/2005 |
| JP | 2006-525062 | 11/2006 |

OTHER PUBLICATIONS

Patent Examination Report No. 1 for corresponding Australian patent application No. 2009316729 dated Feb. 10, 2014, 5 pages.

* cited by examiner

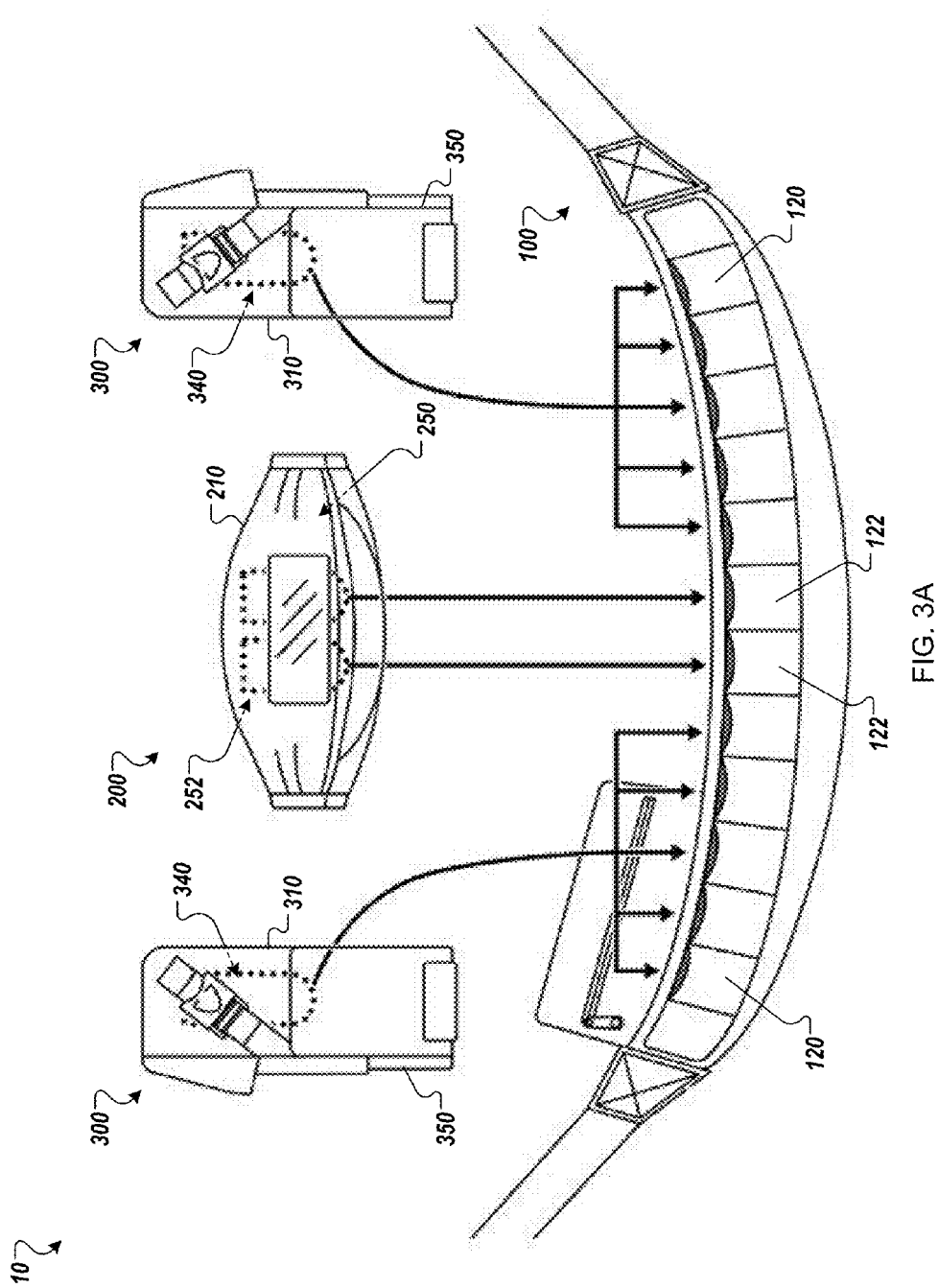

MEDICAL DEVICE ACCESSORY CARRIER

CROSS-REFERENCE TO RELATED APPLICATIONS

This application claims priority under 35 U.S.C. §119(e) to U.S. Provisional Patent Application Ser. No. 61/115,796, entitled "Medical Device Controller and Accessory Carrier," and filed on Nov. 18, 2008, the entire disclosure of which is incorporated herein by reference.

TECHNICAL FIELD

This disclosure relates to medical device carriers that retain accessories, such as controllers and batteries, associated with a medical device.

BACKGROUND

The human heart is a pump—a complex and critical pump. As with any pump, the heart can become clogged and wear out over time. When wear and damage to the heart become sufficiently serious, the owner of the heart is said to have suffered severe heart failure. In such a situation, it is often necessary for the person to receive mechanical assistance for the heart or to receive a heart transplant. Where the person is scheduled to receive a transplant, mechanical assistance may be a choice of therapy until a donor heart is available.

Blood pumps are commonly used to provide mechanical assistance to the left ventricle of the heart. Ventricular assistance may be provided by an implantable pump that is connected in parallel with the person's cardiovascular system. A controller that is external to the body may regulate the pump. Additionally, the controller and the pump may require power from a source such as one or more batteries. For a patient to maintain mobility, such external components can be carried by the patient.

SUMMARY

Improving the ability of a user with a medical device (e.g., an implanted medical device) to move around and to accomplish normal daily tasks (e.g., showering, shopping, going to work, and the like) can significantly improve the psychological condition of a user. External accessories associated with a medical device, however, may be bulky and reduce the ability of the user to accomplish normal daily tasks. A carrier system for one or more external accessories, however, can improve the mobility and the comfort of the user of an implanted medical device by holding the one or more external accessories adjacent to the user in a way that prevents damage to the medical device or any of the external accessories. Accordingly, a number of carrier systems for medical device accessories are described herein.

According to a first aspect, a carrier system for carrying medical device accessories includes a first battery pouch to enclose at least a portion of a first battery and a garment to be worn about a torso. The garment includes a plurality of accessory connection features adapted to allow for adjustable attachment of at least the first battery pouch and for adjustable attachment of a medical device controller that is electrically connected to a medical device. The controller is configured to control an implanted medical device. The instantly described carrying systems is designed to give additional mobility to someone having an implanted medical device requiring attachment to a controller and/or a battery that are not implanted into the body cavity.

The first battery pouch can be adapted to be attached to a plurality of accessory connection features so that a user can adjust an attachment location of the first battery pouch to the garment. Each of the plurality of accessory connection features can also be adapted for attachment of the controller.

The first battery pouch can be attached to a generally u-shaped first clip adapted to fit over at least a portion of one or more of the accessory connection features. In some embodiments, the generally u-shaped first clip is rotatably attached to the first battery pouch. A rotatably attached generally u-shaped clip can allow for the battery pouch to rotate relative to the garment.

The accessory connection features can include two or more pockets. In some embodiments, the carrier system includes 4 or more pockets. In other embodiments, the carrier system includes at least 10 pockets. Each pocket can be adapted to receive a clip to allow for battery pouches and/or controllers having a clip to be removably attached to the garment. For example, the carrier system can further include a second battery pouch to enclose at least a portion of a second battery. The second battery pouch can have a generally u-shaped rotatable clip adapted to be at least partially received within one of the pockets of the carrier system. The carrier system can also include additional battery pouches. By allowing each battery pouch and/or a controller to be selectively attached to each of the accessory connection features of the garment, a user can independently adjust an attachment location for each of the batteries and the controller to maximize comfort.

The carrier system may include a controller pouch to enclose at least a portion of a medical device controller.

In some embodiments, a carrier system includes a plurality of adjustment straps that are each adapted to couple battery pouches and/or controllers to the garment. For example, the carrier system can include a first adjustment strap adapted to couple a first battery pouch to the garment, a second adjustment strap adapted to couple a controller to the garment, and a third adjustment strap adapted to couple a second battery pouch to the garment. For example, the carrier system can be in the form of a holster vest. In other embodiments, the carrier system can be in the form of a utility belt.

According to a second aspect, a carrier system for carrying batteries of a medical device includes a garment to be worn about a torso, a first battery pouch to enclose at least a portion of a first battery, and a generally u-shaped first clip rotatably attached to the first battery pouch and adapted to fit over a portion of the garment. The first clip can permit the first battery pouch to rotate relative to the garment.

The carrier system can, in some embodiments, include a second battery pouch to enclose at least a portion of a second battery. The second battery pouch can be rotatably attached to a generally u-shaped second clip. The second clip can be adapted to fit over a portion of the garment. The second clip can permit the second battery pouch to rotate relative to the garment.

The garment can include a plurality of accessory connection features each adapted for attachment of the first battery pouch or the second battery pouch. The garment can include at least twice as many accessory connection features as the number of battery pouches of the carrier system.

According to a third aspect, a carrier system for carrying batteries of a medical device includes a pouch to enclose at least one battery and a medical device controller and a strap removably coupled to the pouch for support. The pouch is configured to hold at least the one battery in a fixed location relative to the medical device controller. The pouch includes an opening, through which a wire connected to an enclosed medical device controller can pass, for keeping an enclosed medical device controller in electrical connection with an implanted medical device. For example, the carrier system can be a consolidated bag and/or a shower bag.

The pouch can be adapted to hold an enclosed battery and an enclosed medical device controller in a substantially planar configuration. The pouch can also be adapted to enclose at least a second battery and to hold an enclosed medical device controller and at least two enclosed batteries in a substantially planar configuration.

The pouch can be water resistant or waterproof. A water resistant or water proof pouch can, in some embodiments, allow for a user to take a shower with a controller and one or more batteries in the pouch. In some embodiments, at least a portion of the pouch is translucent or transparent to allow the medical device controller to be visible through the pouch. The translucent or transparent portion of the pouch can be adapted to allow a user to manipulate the medical device controller though the pouch to input data. The carrier system can further include a flap adapted to conceal the translucent portion of the pouch to conceal any enclosed medical device controller.

The details of one or more embodiments of the carrier system are set forth in the accompanying drawings and the description below. Features, objects, and advantages of the carrier system will be apparent from the description and drawings, and from the claims.

DESCRIPTION OF DRAWINGS

FIG. 3A is a front view of a modular medical device accessory carrier and uncoupled modular devices, in accordance with some embodiments.

Like reference symbols in the various drawings indicate like elements.

DETAILED DESCRIPTION OF ILLUSTRATIVE EMBODIMENTS

In some embodiments, a medical device accessory carrier system is configured to retain accessories associated with a medical device, such as a left and/or right ventricular assist device (VAD). This left and/or right ventricular assist device (VAD) can be implanted into either the abdomen or the thorax. Exemplary accessories that can be carried and retained by a carrier system may include batteries, controllers, displays, input devices, and the like. The carrier system is configured to hold accessories for operation of the medical device, while giving the user relative freedom of movement. For example, a user with an implanted VAD may be connected to an external controller and power source for proper functioning of the VAD. In some of these examples, power for the VAD may come from a substantially immovable source, such as a standard wall socket, where the user is tethered to the power source by a cord, thus limiting the distance that the user can travel. If the user desires to travel farther (e.g., leave his bedroom, his home, or the like), one option may be to use a portable controller and power source. Because the VAD may be attached to the controller and power source, a carrier system holding these accessories can be configured to maintain the proper connections while enabling freedom of movement while these accessories are being worn by the user.

Modular Belt

Figure 1:
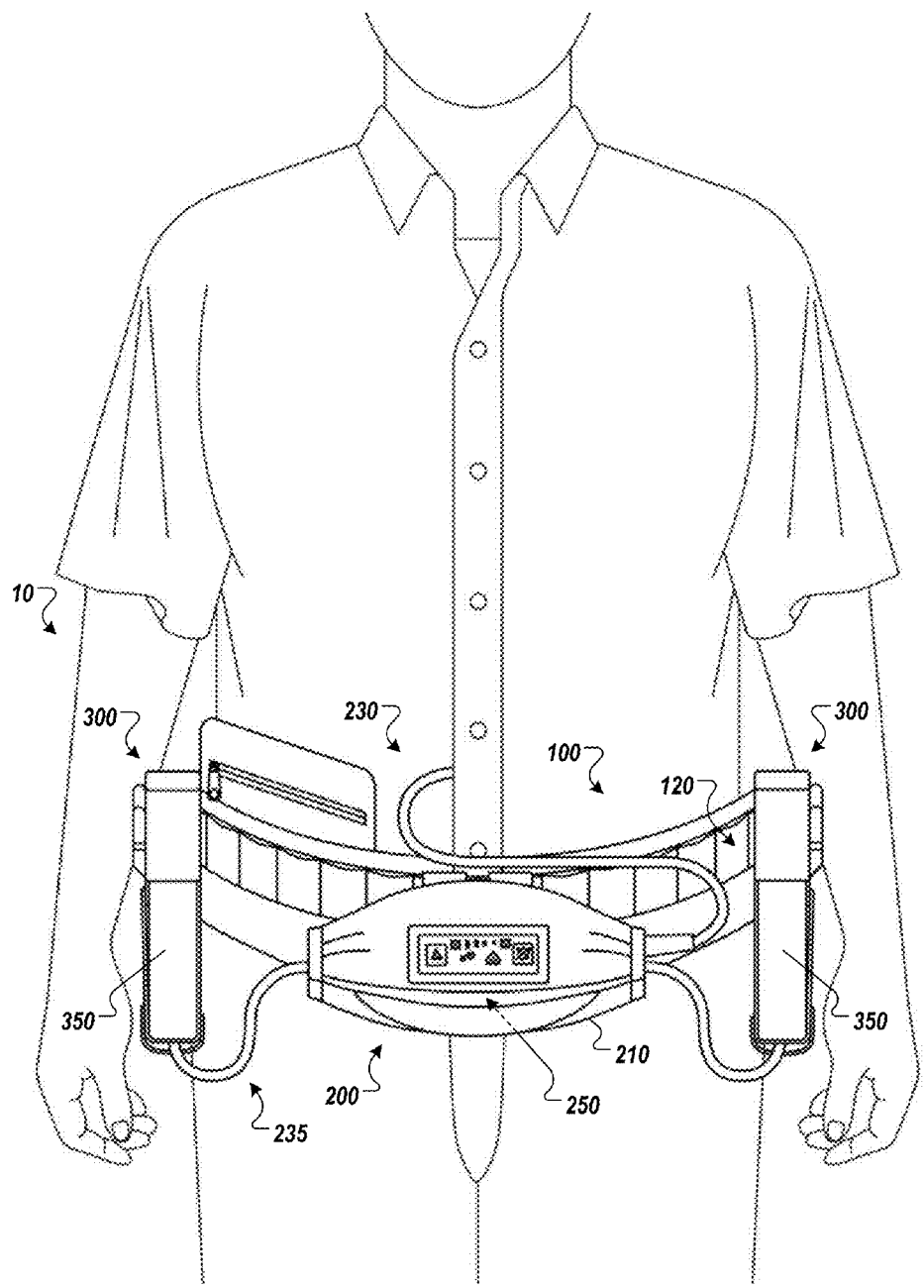
FIG. 1 is a front view of a user wearing a modular medical device accessory carrier, in accordance with some embodiments.
Figure 2:
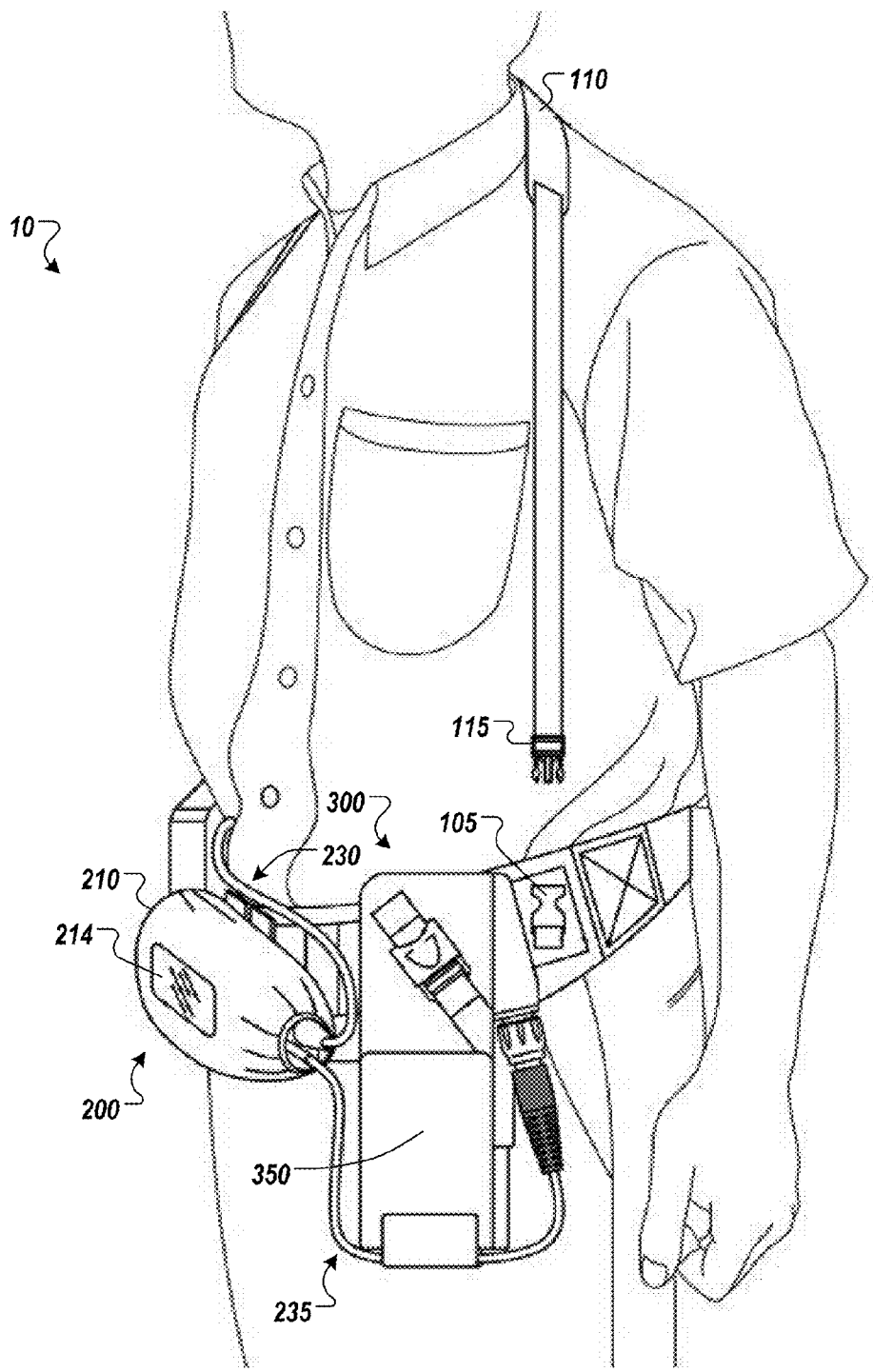
FIG. 2 is a side view of a user wearing a modular medical device accessory carrier including optional neck strap, in accordance with some embodiments.

A medical device accessory carrier system 10 can be a modular belt 100, to be worn around the waist of a user, for holding and transporting accessories associated with a VAD. Examples of modular belts are depicted in FIGS. 1 and 2. FIG. 1 is a front view of a user wearing a modular medical device accessory carrier. FIG. 2 is a side view of a user wearing a modular medical device accessory carrier including optional neck strap. The modular belt 100 can hold one or more controller assemblies 200 (e.g., including a controller device 250), one or more battery assemblies 300 (e.g., each including one or more batteries 350), and any associated electrical connections (described in more detail below) in close proximity to an implanted medical device and/or an associated percutaneous opening. The modular belt 100 can be configured to carry accessories, such as the controller device 250 and the batteries 350, so as to reduce occurrences that could interfere with the function of the implanted VAD. For example, the modular belt 100 is configured to secure the controller assembly 200 and the battery assemblies 300 such that they do not separate from the modular belt 100 unintentionally, thereby causing damage to the accessories retained by the modular belt 100 (e.g., the controller device 250, the batteries 350, and the like). In another example, the modular belt 100 is configured to maintain the battery assemblies 300 at a substantially fixed distance from the controller assembly 200 and to maintain the controller assembly 200 at a substantially fixed distance from the implanted VAD such that power and electrical leads 230 and 235 do not become entangled, damaged, or separated from the VAD, the controller device 250 or the batteries 350. In some embodiments, the controller assembly 200 includes a water resistant or waterproof controller pouch 210, for example, that may reduce or eliminate exposure of the controller device 250 to fluids, contaminants, moisture, and the like.

The carrier system 10 can include an optional neck strap 110 for coupling with the modular belt 100 to shift at least a portion of the weight of the carrier system 10 away from the lower torso (e.g., by connecting the carrier system 10 to a portion of the patient's shoulders or neck). The neck strap 110 (shown in FIG. 2) can de draped around the back of the neck and extend substantially downward across the front of the torso. In one embodiment, the neck strap 110 couples to the modular belt 100 using one or more clips 115, attached to the ends of the neck strap, that mate with corresponding clips 105 attached to the belt 100 and located proximate to the user's hips when the belt 100 is worn by the user. In other embodiments, the corresponding clips 105 can be included at other locations of the belt 100. The optional neck strap can also be selectively used to fully support the weight of the modular belt 100. For example, a user can use the bathroom or change clothes while maintaining the controller assembly 200 and the battery assemblies 300 in a desired location by using the neck strap 110 as described above and releasing the modular belt 100. In this way, the modular belt 100 no longer fully surrounds the user's waist and is fully supported by the neck strap 110. The user is then free, for example, to use the bathroom, change pants, and the like, while maintaining the modular belt 10 and associated medical device accessories in a desired location.

The modular belt 100 can be adapted to allow for user-configuration of accessories associated with a medical device (e.g., to increase the comfort level of a user). For example, FIG. 3A is a front view of a modular medical device accessory carrier and uncoupled modular devices. The modular belt 100 can include a plurality of accessory connection features (e.g., vertical pockets 120) configured to reversibly receive corresponding features of the medical device accessories or accessory holders. Each of the pockets 120 can include an opening 121 located in the top portion of the pocket 120 that can receive one or more clips 252 attached to the accessories and/or accessory holders. For example, the controller device 250 depicted in FIG. 3A has two clips 252 attached to a back side of the controller device 250 such that when a user couples the controller device 250 to the belt 100, the user is not limited to one specific location on the belt 100, but instead can select from a plurality of possible connection points (e.g., two adjacent, empty pockets 120). Because the belt 100 can include a plurality of the pockets 120 (e.g., between 2 and 100 pockets, at least 4 pockets, at least 10 pockets, 24 pockets, 14 pockets and the like) located around at least a portion of the circumference of the belt 100, the user can, for example, select different pockets or different sets of pockets to select different attachment points for each accessory. For example, as shown in FIG. 3A, a set of two pockets 122, located substantially in the center of the modular belt 100, can be used for attaching the controller assembly 200 so that the controller assembly 200 is located about waste-high in the front of the user when the belt 100 is worn. The user can choose to position the controller assembly 200 in this location for exemplary reasons such as, even distribution of the weight of the controller assembly 200, ready access to the controller device 250, and the like.

Each of the empty pockets 120 can also each receive clips attached to other accessories. Clips 340 (described in more detail in connection with FIG. 6) are attached to battery assemblies 300 (e.g., attached to a back side of a battery pouch 310). The user can thus also select any of the pocket locations 120 to couple the battery assemblies 300 and can choose the location for exemplary reasons such as, even distribution of the weight of the battery assemblies 300, ready access to the battery assemblies 300, disguising the battery assemblies 300 from the general public, locating the battery assemblies 300 so as to not interfere with the user or the user's activities, and the like. Generally speaking, the controller assembly 200 and the battery assemblies 300 can be positioned in locations that result in increased comfort for the user.

The controller assembly 200 can be coupled to a location on the belt 100 that reduces interference with the user's activities, increases comfort of the user, decreases the chance of damage to the controller device 250, and the like. For example, the controller assembly 200 may be coupled to the front of the belt 100, as depicted in FIG. 1. In this location, the controller assembly 200 is readily accessible to the user and the weight of the controller assembly 200 may be more favorably distributed. In other instances, this location may not be desirable when the user performs a task such as carrying a bag of groceries. For example, the user may wish to hold the bag of groceries securely between one arm and his torso. This position may cause the bag to interfere with the controller assembly 200, one of the battery assemblies 300, the electrical leads 230 and 235, and the like. Due to the plurality of pockets 120 on the modular belt 100, the user can readily detach and reattach the controller assembly 200 and/or one or both battery assemblies 300 to reposition the accessories to a side of his torso (e.g., the right side), to reduce interference with the bag of groceries. Under some circumstances, for example, when a user is not performing tasks that may interfere with the controller assembly 200 and/or the battery assemblies 300, the user may again reposition the accessories attachment locations on the modular belt 110 to provide increased comfort to the user, such as by evenly distributing the weight of the controller assembly 200 and battery assemblies 300 as shown in FIG. 1.

Figure 3B:
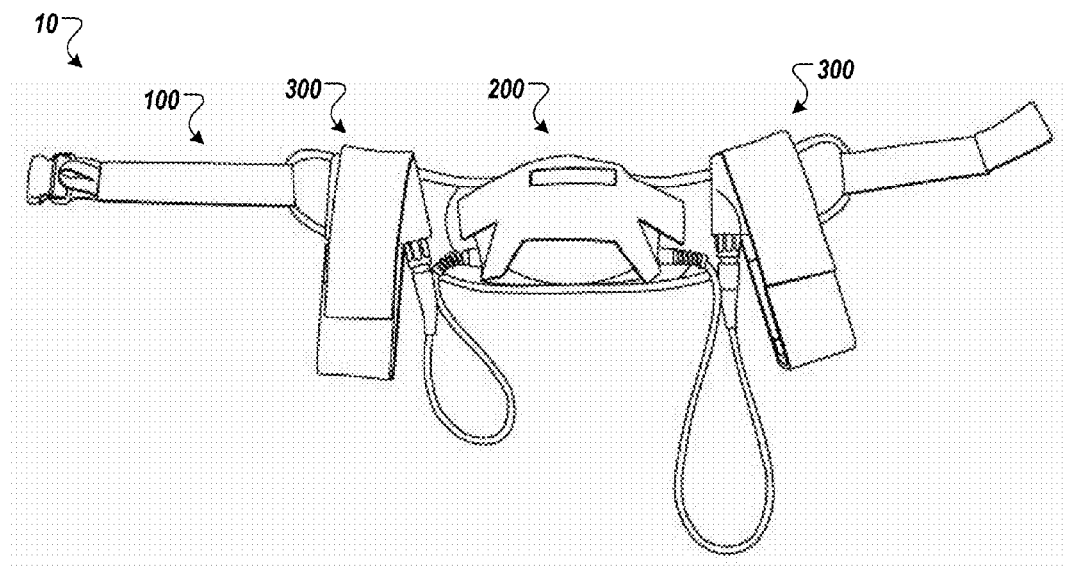
FIGS. 3B-3C are front views of a modular device accessory carrier including coupled modular devices in a variety of orientations, in accordance with some embodiments.
Figure 3C:
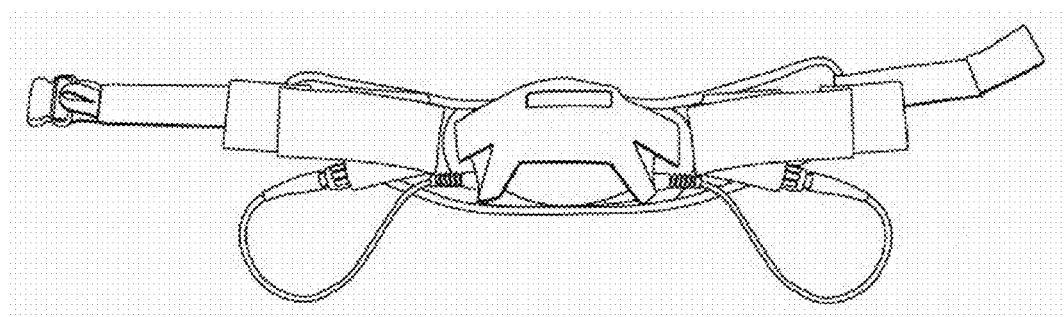

The accessory carrier system 10 can be also include features that increase the comfort level of a user by allowing the user to adjust the orientation of accessories associated with an implanted medical device without detachment from the modular belt 100. In one example, each of the battery assemblies 300 include a rotating clip 340 (described in more detail below in connection with FIG. 6). The rotating clip allows the battery pouch 310 to be rotatably coupled to the belt 100 to allow for a variety of orientations between the battery pouches 310 and the modular belt 100. FIGS. 3B-3C are front views of a modular device accessory carrier including coupled modular devices in a variety of orientations, in accordance with some embodiments. Allowing for different orientations may allow for increased user comfort. In some embodiments, the rotating clip 340 can allow for unrestricted rotation, whereby gravity and interaction with other objects will generally dictate the orientation of the battery pouch 310. For instance, in a standing position, the battery pouch 310 can be maintained in the substantially vertical orientation shown in FIGS. 1, 3B due to the forces of gravity. When the user sits down, the battery pouches 310 are substantially free to rotate with respect to the belt 100 to an orientation dictated by the movement of the user's body relative to the seat and other adjacent objects. The user can also manually rotate one or both battery pouches 310 to position that reduces the pressure applied on the user by the battery assembly 300 (e.g., to a substantially horizontal orientation depicted in FIG. 3C). In examples where a portion of the battery assemblies 300 does not rotate relative to a user, the battery assemblies 300 can exert increased pressure on the user, such as on the side of the torso, the hip, the abdomen, and the like, when the user changes positions (e.g., sits down). When free to rotate, the battery pouches 310 can be rotated to a position that decreases the pressure exerted on the user. The battery assembly 300 can be configured to provide minimal frictional resistance to rotational movement. In other embodiments, frictional resistance to rotational movement can be used to dampen the movement of the battery assemblies due to normal physical activity. The battery assembly 300 can, in some embodiments, include locking mechanisms that can be selectively activated or deactivated by a user. For example, rotating clip 340 can have a spring loaded locking device to allow a user to selectively rotate the battery pouch 310 between different locked orientations. The battery assembly, in some embodiments, can include a ratcheting mechanism to allow for preferential rotational movement in one direction. A user could then actuate the ratcheting mechanism to reorient the battery pouch 310. A battery assembly 300 can include a locking mechanism that can be selectively engaged to allow for an unrestricted rotational movement option and a restricted rotational movement option.

Figure 4:
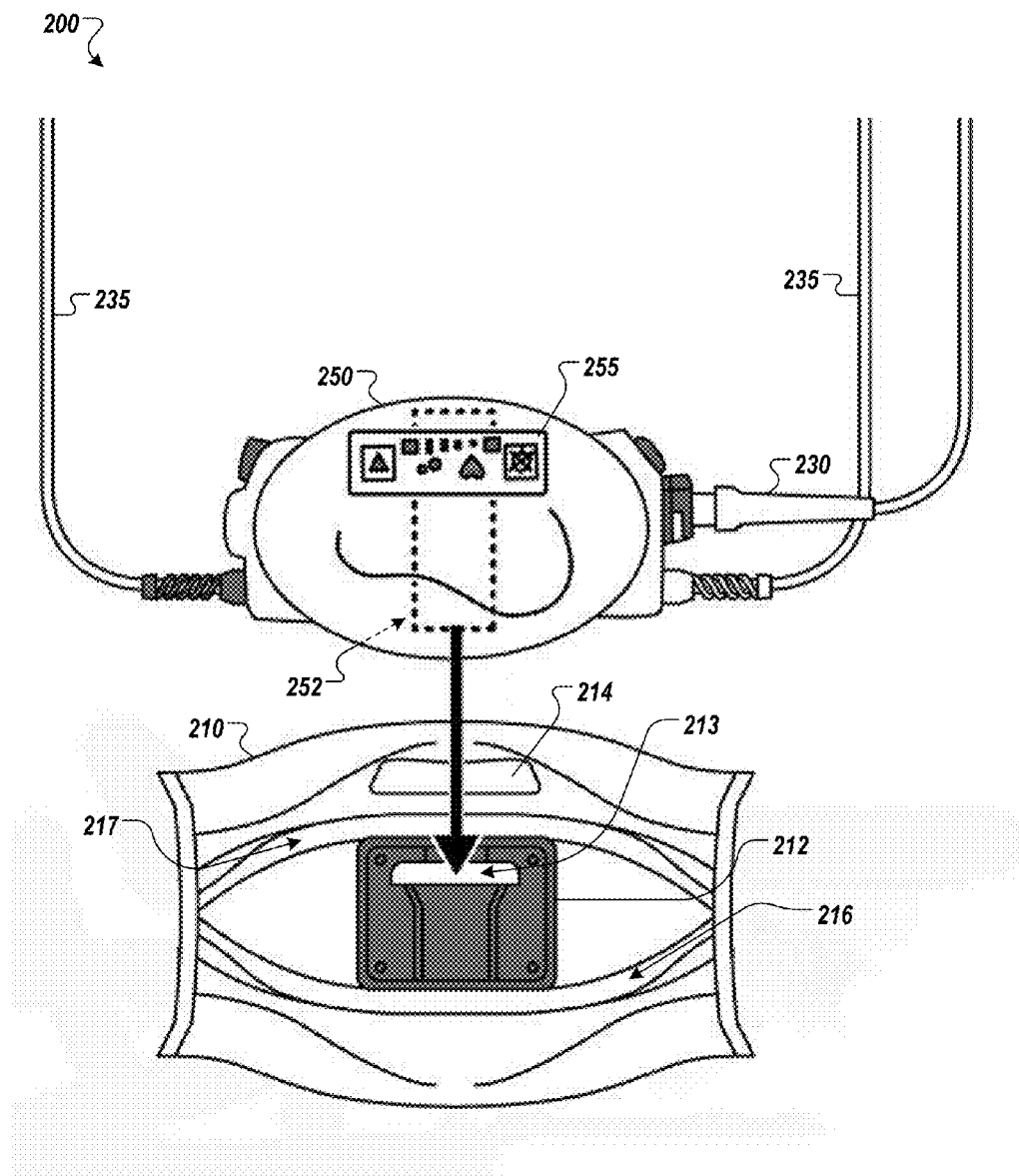
FIG. 4 is a top view of a medical device controller pouch and an uncoupled device controller, in accordance with some embodiments.

A controller pouch 210 can be used to at least partially enclose the controller device 250, for example, to protect it from contaminants, fluids, moisture, and the like. For example, FIG. 4 is a top view of a medical device controller pouch and an uncoupled device controller. The controller pouch 210 can include a backing plate 212 and opening 213, both located on the back portion of the pouch 210, which can cooperate with the one or more clips 252 included on the rearward-facing surface of the controller device 250. When placing the controller device 250 in the controller pouch 210, the single clip 252 depicted in FIG. 4 can be inserted through the opening 213 such that when the controller device 250 is enclosed by the controller pouch 210, a portion of the clip 252 is exposed through the rearward-facing surface of the controller pouch 210. In the embodiment depicted in FIG. 3A, the controller device 250 can include two clips 252 that can be inserted through the opening 213. When coupling the controller assembly 200 to belt 100, as depicted in FIG. 3A, the exposed portion of the two clips 252 are placed inside adjacent, empty pockets 120 (such as pockets 122). Thus, a friction fit is accomplished by pinching a portion of the pockets 120 between the exposed portion of the clips 252 and the backing plates 212. In the embodiment depicted in FIG. 4, the controller device 250 can be coupled to the belt 100 using a single pocket 120.

The accessory carrier system 10 can include features for monitoring and controlling the operation of an implanted medical device by the controller device 250 without having to remove the controller device 250 from the controller pouch 210. For example, the controller pouch 210 can include a see-through portion 214 for allowing the user to monitor a display 255 of the controller device 250 while the controller device 250 is enclosed by the pouch 210. In some examples, the see-through portion 214 can include a flexible material such that the input of the controller device 250 (e.g., buttons, a touch-sensitive screen, a membrane keyboard, and the like) can be operated by the user without requiring that the controller device 250 be removed from the controller pouch 210. In other examples, the pouch 210 can be made from polycarbonates, acrylics, ABS, nylon, silicone, styrene, thermoplastic elastomers, thermoplastic polyurethane, and the like.

The accessory carrier system 10 can include features for monitoring and controlling the operation of an implanted medical device by the controller device 250 without having to remove the controller assembly 200 from the modular belt 100. For example, the controller device 250 can be positioned in the pouch 210 in a substantially upside-down orientation such that onlookers viewing the controller assembly 200 from the front of the user (when the belt 100 is worn by the user as depicted in FIG. 1) will see the display 255 upside down. However, by tilting the controller assembly 200 such that the display 255 changes orientation from generally frontward facing to generally upward facing, the user can look down on the display 255 and view it substantially right side up.

The controller pouch 210 can be configured such that the controller device 250 can be enclosed by the controller pouch 210 without having to uncouple electrical leads 230 and 235 from the controller device 250. For example, the controller device 250 can be placed in the controller pouch 210, as described previously, with the clip 252 inserted through the opening 213. When the controller device 250 is located inside the controller pouch 210, the controller pouch 210 can be closed such that the controller device 250 is shielded and the display 255 is visible through the see-through portion 214. A lower flap 216 can be pulled up along the front face of the controller device 250 and an upper flap 217 can be pulled down such that it overlaps at least a portion of the lower flap 216. The upper flap 217 and the lower flap 216 can be secured to each other (e.g., using hook-and-loop fasteners, snaps, one or more zipper assemblies, water-resistant zippers, and the like).

Figure 5:
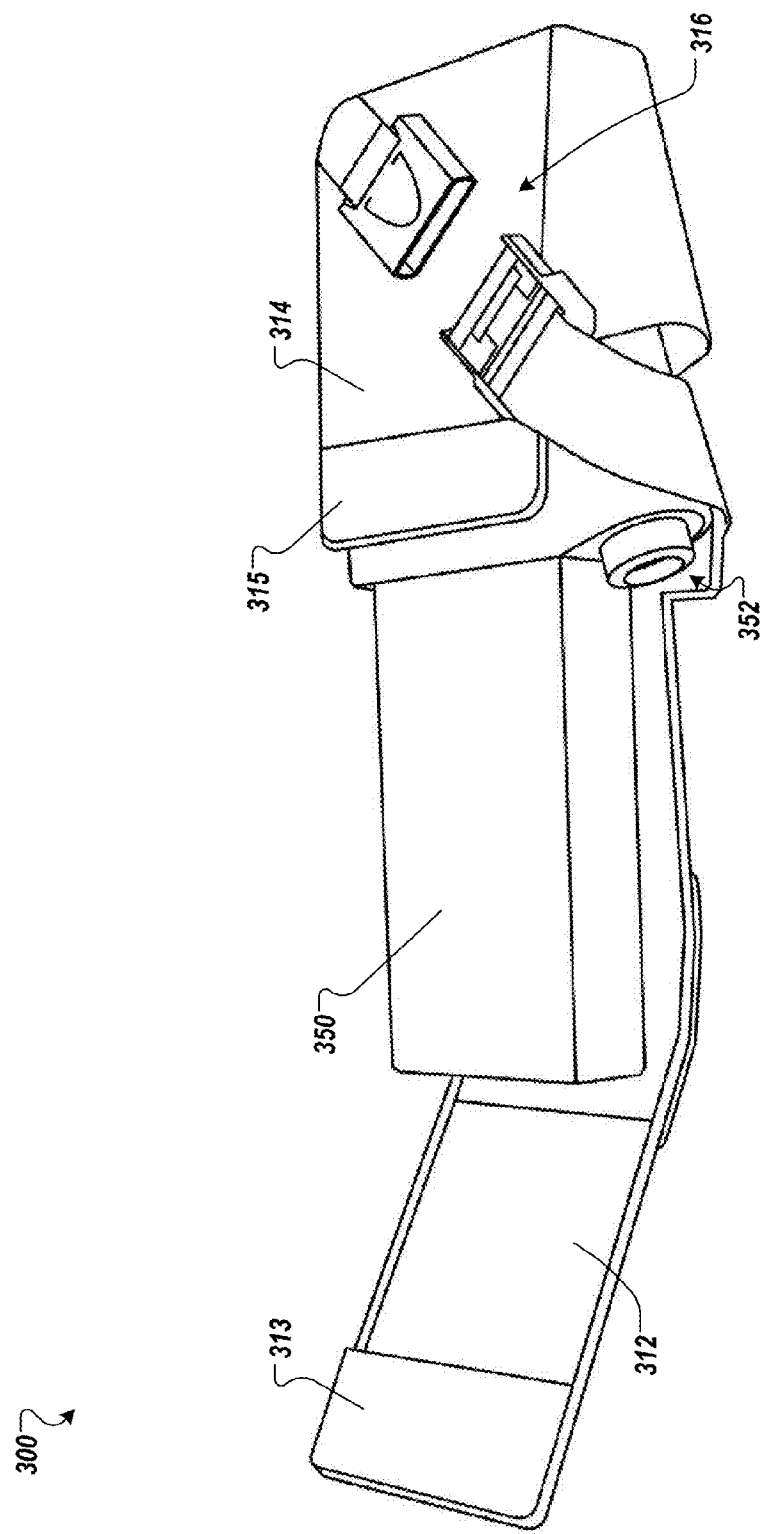
FIG. 5 is a perspective view of a battery container in an open configuration, in accordance with some embodiments.

A battery 350 powering an implanted medical device can be replaced, for example, with a new battery 350 that contains a greater charge. For example, FIG. 5 is a perspective view of a battery container in an open configuration, in accordance with some embodiments. To replace the battery 350, an electrical lead 235 (see FIG. 10A) can be uncoupled from an electrical connector 352 and the battery assembly 300 can be uncoupled from the modular belt 100 (as depicted in FIG. 3A) and placed on a substantially flat surface. To remove the battery 350, a portion of a lower flap 312 can be uncoupled from an upper battery pocket 314. For example, a securing portion 313 of the lower flap 312 can be secured to a underlying portion 315 of the pocket 314 (e.g., with hook-and-loop fastener, snaps, and the like). Applying gentle outward force to the lower flap 312 substantially at the securing portion 313 can cause the securing portion 313 to separate from the underlying portion 315, thus transitioning the lower flap 312 to the open configuration shown. The buckle assembly 316 can be separated and the battery 350 to allow a user to remove the battery 350 from the battery pouch 310 (e.g., to the left in FIG. 6). In some embodiments, prior to removing the battery 350, a release button (not shown) can be pressed allowing at least a portion of the battery 350 to slide out of the battery pouch 310. A different battery can then be installed in the battery pouch 310 by reversing the removal steps. For example, a fully recharged battery can be inserted into the battery pouch 310, the buckle assembly 316 can be united, and the lower flap 312 can be closed, causing the portions 313 and 315 to unite. The battery 350 can also be replaced while the battery assembly 300 is coupled to the belt 100 (described in connection with FIGS. 10A-B), so a user can choose which method is most convenient.

Figure 6:
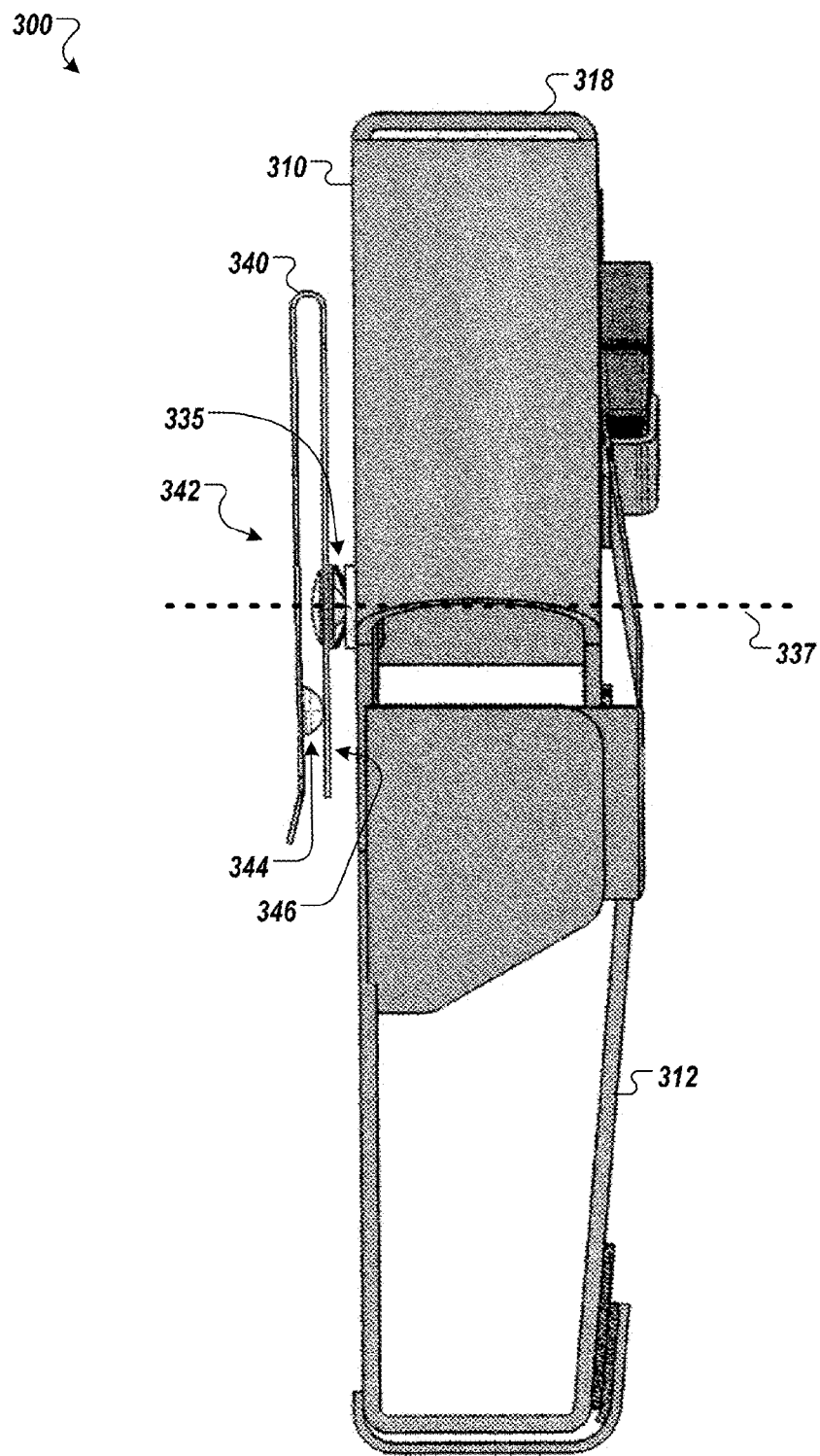
FIG. 6 is a side view of a battery holder including a swivel mount, in accordance with some embodiments.

The battery assembly 300, as noted above, can include a clip 340 rotatably coupled to the rearward facing surface of the battery pouch 310. For example, FIG. 6 depicts a side view of a battery holder including a swivel mount. The battery assembly of FIG. 6 includes a rotating assembling 335 that allows the battery pouch 310 to rotate around an axis 337. Clip 340 can be attached to an article of clothing (e.g., a belt, a pocket, the wasteband of a pair of pants, the pockets 120 of the modular belt 100 shown in FIG. 3A, and the like) such that the battery pouch 310 and an enclosed battery (not shown) can rotate relative to the article of clothing while being securely coupled to the article of clothing. When coupling the battery assembly 300 to the belt 100 as shown in FIG. 3A, the outermost portion 342 of the clip 340 is placed inside one of the pockets 120. Thus, a friction fit is accomplished by pinching a portion of the pocket 120 between the outermost portion 342, specifically a protrusion 344, and an innermost portion 346. In some embodiments, the battery pouch 310 can rotate relative to clip 340 with minimal frictional interference so that when the battery assembly is coupled to the modular belt 100 using the clip 340, the battery pouch 310 can rotate around the axis 337 and relative to the modular belt 100 (as depicted in FIG. 3C) with minimal force applied to the battery assembly 300. For example, when a user is in a standing position, the user can rotate the battery pouch 310 to the substantially vertical orientation depicted in FIGS. 1, 3B, and 6.

The battery pouch 310 can be maintained in the vertical orientation by, for example, friction associated with the rotating assembly 335, detents in the rotating assembly 335, spring loaded locking elements, and the like. The forces maintaining the battery pouch 310 in the desired orientation can be great enough to overcome the forces associated with gravity and general movement by the user, but can be easily overcome by the user when manipulating the battery pouch 310 to change the orientation of the battery pouch 310. For example, in anticipation of changing to a seated position, the battery pouch 310 can be actively manipulated to a non-vertical orientation (e.g., 90 degrees from vertical, 45 degrees from vertical, 31.4 degrees from vertical, and the like) by the user. The user can rotate the battery pouch 310 to a new orientation (such as the substantially horizontal orientation depicted in FIG. 3C) that is predicted by the user to be more comfortable once the user changes to the seated position. Once seated, the user can further rotate the battery pouch relative to the modular belt 100 to increase the comfort of the user. Frictional forces can also dampen the rotational movement of the battery pouch due to normal physical activity. In another example, passive forces applied to the battery pouch 310 by the user (e.g., by the user's hip, stomach, torso, legs, and the like) when the user changes positions can automatically cause the battery pouch 310 to rotate to an orientation that reduces the forces applied to it by the user's anatomy, thus automatically decreasing the discomfort associated with the battery assembly 300.

Figure 7:
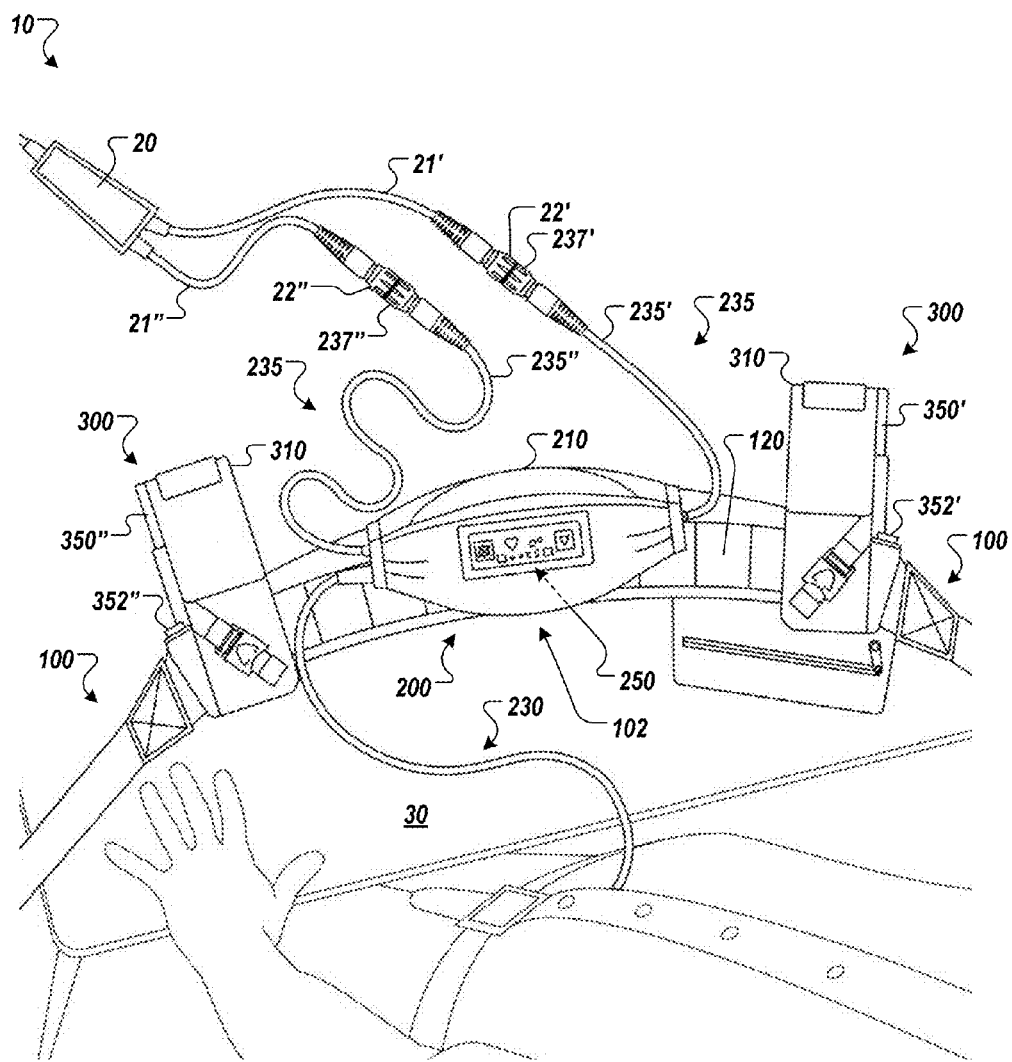
FIG. 7 is a top view of a modular medical device accessory carrier positioned on a table, in accordance with some embodiments.

FIG. 7 is a top view of a modular medical device accessory carrier positioned on a table. Accessories associated with an implanted medical device (not shown) may limit the movement of a user. Exemplary accessories that may limit a user's movement can include a non-portable controller device, the controller device 250, a power source including a power cord plugged into a conventional wall socket, and the like. The user may employ the medical device accessory carrier system 10, including batteries 350' and 350" to achieve freedom of movement not obtainable without use of the system 10. Briefly, in use, the user can place the modular belt 100 on a substantially flat surface 30, as shown in FIG. 7, with the pockets 120 facing upwards. The user can couple one of the battery assemblies 300 to the belt 100 by inserting the distal end of the included clip 340 into any one of the available pockets 120 located around the circumference of the belt 100 (see FIG. 3A). The user can make the choice of which pocket 120 to couple the battery pouch 310 to based on, for example, convenience. The user can couple a second battery assembly 300 to the belt 100 in a manner similar to the first. With the battery assemblies 300 coupled to the modular belt as shown in FIG. 7, the user can insert and secure one battery (e.g., the battery 350', the battery 350", and the like) into each of the pouches 310 as described in connection with FIG. 5.

The user can also place the controller device 250 inside the controller pouch 210 as described in connection with FIG. 4. When inside the controller pouch 210, the user can see the display 255 of the controller device 250 and can operate the input of the controller device 250. Using the clips 252 (see FIG. 3A) on the back of the controller device 250, the user can secure the controller assembly 200 to the modular belt 100 as depicted in FIG. 7. Due, at least in part, to the presence of the two power leads 235, the controller device 250 can be transferred from a fixed power supply, such as a power supply 20, to a portable power supply (e.g., batteries) without interrupting the power supply to the controller device 250 or the medical device electrically connected to the controller device 250 via the electrical lead 230, which is connected to the implanted medical device and exits from the user's body cavity. In another embodiment, the accessory carrier system can be used for carrying a controller system or associated power supply components for an implanted medical device, without a lead exiting the body cavity, that receives power through a means of transferring energy transcutaneously. In use, a user can uncouple one of the electrical leads 235 (e.g., an electrical lead 235') from a power supply lead 21' at connectors 237' and 22'. The connector 237' can then be coupled to a connector 352' on a battery 350'. While the electrical lead 235' is uncoupled from both the power supply 20 and the battery 350', power can still be received by the controller device 350 through the other electrical lead 235 (e.g., an electrical lead 235"). Once the lead 235' is reconnected to a power source (e.g., the battery 350'), a connector 237" can be uncoupled from a connector 22" of a power supply lead 21" and coupled to a connector 352" of a battery 350". When each of the electrical leads 235 is connected to a battery (e.g., the batteries 350' and 350"), the user can wear the modular belt 100 to achieve a greater freedom of mobility than when he was connected to non-portable power source 20.

Still referring to FIG. 7, to wear the modular belt 100, the user can stand adjacent to the flat surface 30 and pull the carrier system 10, including the controller assembly 200 and the battery assemblies 300, towards himself, until a top portion 102 comes in contact with the user, substantially at waist-high level. The ends (not shown) of the modular belt 100 can then be pulled around his waste and connected via one or more connector with at least one end of the modular belt 100, while a portion of the weight of the carrier system 10 and attached accessories is still being supported by the flat surface 30. Backing slightly away from the table will allow a lower portion 104 to drop from the table and hang substantially vertically below the upper portion 102 until the carrier system 10 is substantially in the orientation shown in FIG. 1. The optional neck strap 110 can be attached, as described in connection with FIG. 2, to help distribute the weight of the modular belt 10 and the associated accessories before or after the process of connecting the ends of the modular belt 100 around the waste of the user.

When the modular belt is worn by the user, as depicted in FIG. 1, the user may adjust the positioning of the controller assembly 200, the battery assemblies 300, and the like. For example, the user can pull upwards on the controller assembly 200 until the clips 252 separate from the corresponding pockets 120 to which they are coupled. Once uncoupled from the pockets 120, the clips 252 can be coupled to any of the available pockets 120, thus allowing the user to position the controller assembly 200 in a position that he feels is most convenient. Similarly, the battery assemblies 300 can be moved to the pockets 120 that are most convenient for the user.

Holster Vest

Figure 8A:
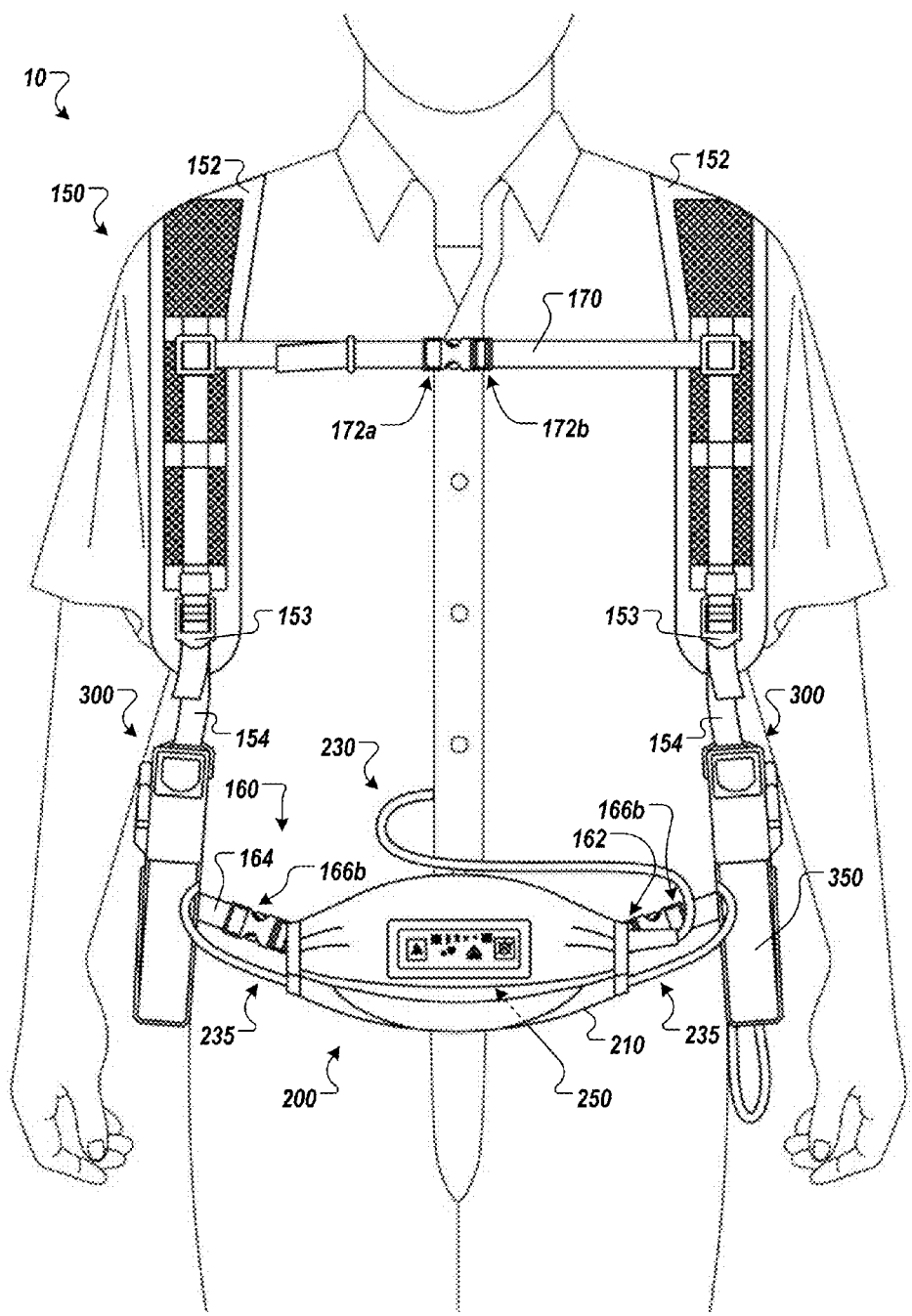
FIG. 8A is a front view of a holster vest embodiment of a medical device accessory carrier worn by a user, in accordance with some embodiments.

The device accessory carrier system 10 can include a holster vest 150 that can be worn by a user and can support at least a portion of the weight of the battery assemblies 300. For example, FIG. 8A is a front view of a holster vest embodiment of a medical device accessory carrier worn by a user. The holster vest 150 can include two shoulder strap assemblies 152 that each drape over one shoulder of the user and extend generally vertically over the torso and the back near the side of the user. A battery adjusting strap 154 can be coupled to the front and back of each strap assembly 152 and can each engage a battery assembly 300 at approximately the center of the strap 154 to at least partially support the battery assembly 300 substantially near the hip of the user allowing for adjustment of the height of the battery assembly 300. This is described below, in more detail, in connection with FIG. 9.

Figure 8B:
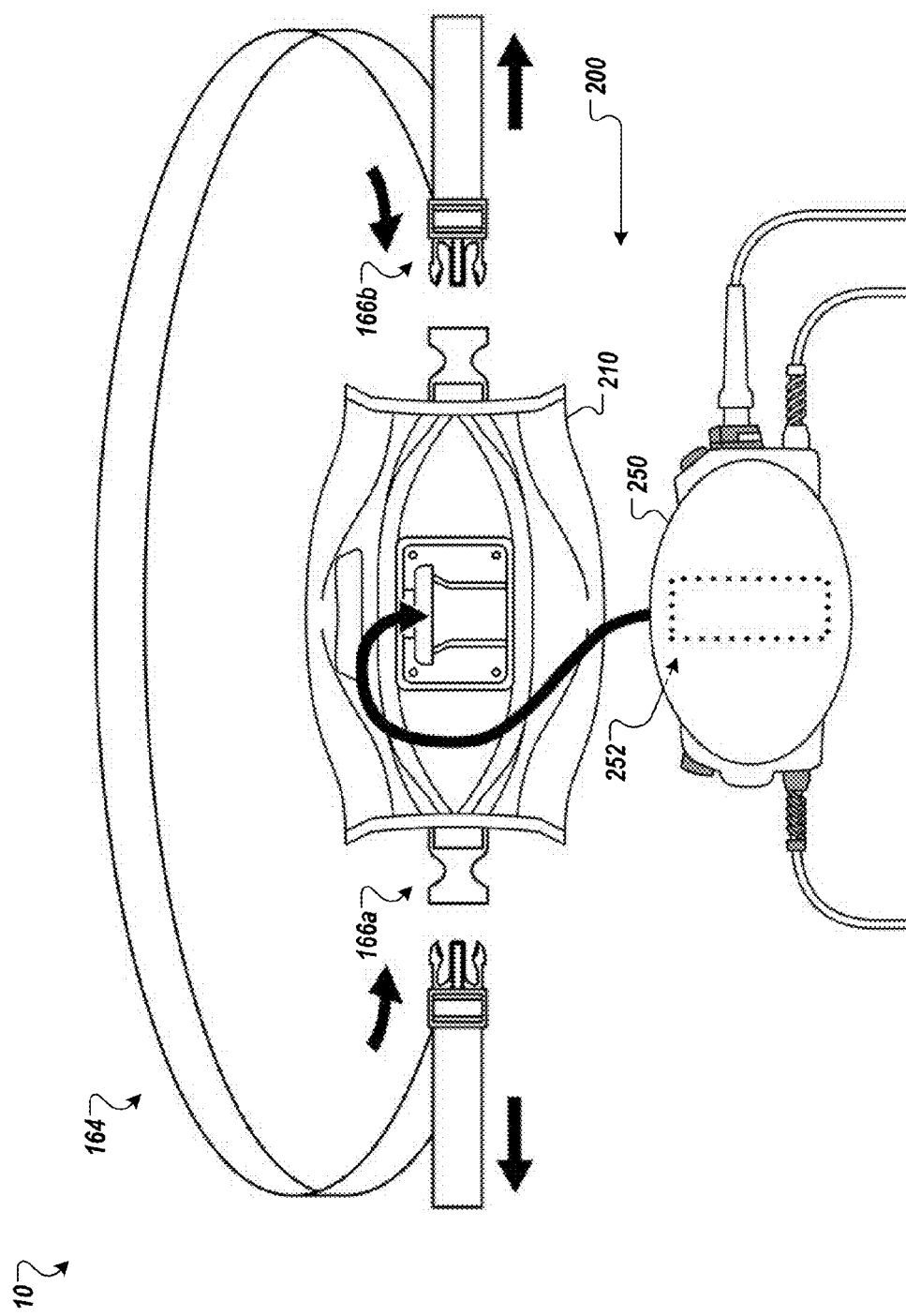
FIG. 8B is a front view of a controller assembly being coupled to a wasteband strap, in accordance with some embodiments.

The holster vest carrier system 10 includes an adjustable waist-strap 160 that can be worn generally around the waist of a user. The waist-strap assembly 160 can include straps 162 and 164, where the controller assembly 200 can be coupled to the strap 162 using the clips 252 (see FIG. 3A). The strap 164 can wrap around a majority of the user's waist and the straps 162 and 164 can be coupled using snap-connectors 166a and 166b to encircle the user's waist. The waist-strap assembly 160 can also engage the battery assemblies 300 substantially maintaining them against the user's hips. In some embodiments, such as depicted in FIG. 8B, the strap 164 can wrap around a majority of the user's waist, engage the clips 340 of the battery assemblies 300 (not shown) and couple to the controller pouch 210 (e.g., via snap-connectors 166a and 166b) to encircle the user's waist.

In one example, the waist-strap assembly 160 can be worn by the user such that waist strap 162 and coupled controller assembly 200 are positioned in the front of the user at about waist height. The waist-strap assembly 160 can be adjusted (e.g., by adjustment portions on the strap 162, the strap 164, and the like) such that the overall diameter of the waist-strap 160 is configured as desired by the user. Further adding to the comfort of the user, the waist strap 160 can include stretchable materials, such as elastic. In some embodiments, the vest 150 can include a chest strap 170 connecting the two shoulder strap assemblies 152 and crossing substantially horizontally across the user's chest. The chest strap 170 can include snap connectors 172a and 172b that, when connected, limit the outward lateral movement of the shoulder strap assemblies keeping them from falling off of the user's shoulders.

Figure 9:
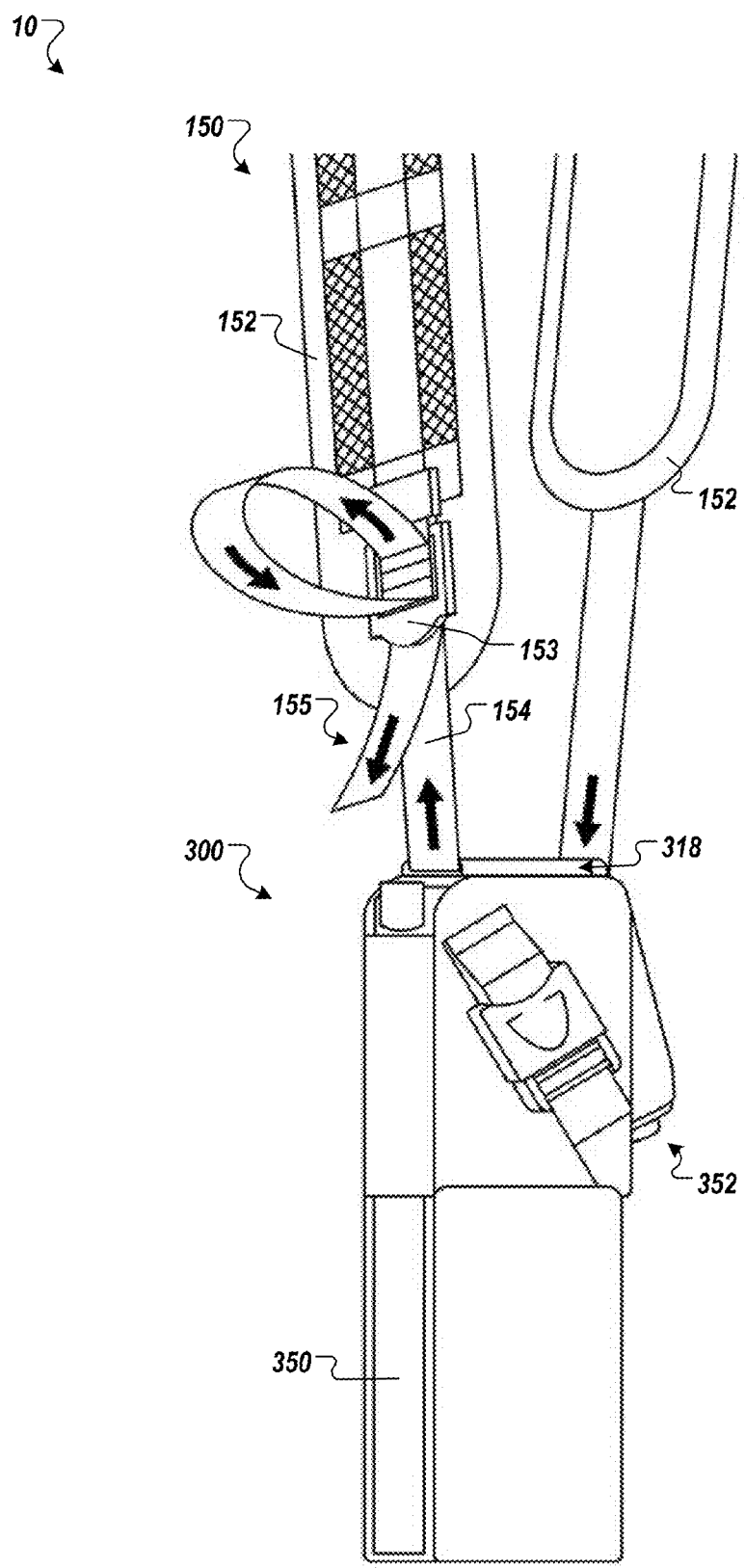
FIG. 9 is perspective view of a battery assembly coupled to a portion of the medical device carrier of FIG. 8A, in accordance with some embodiments.
Figure 11:
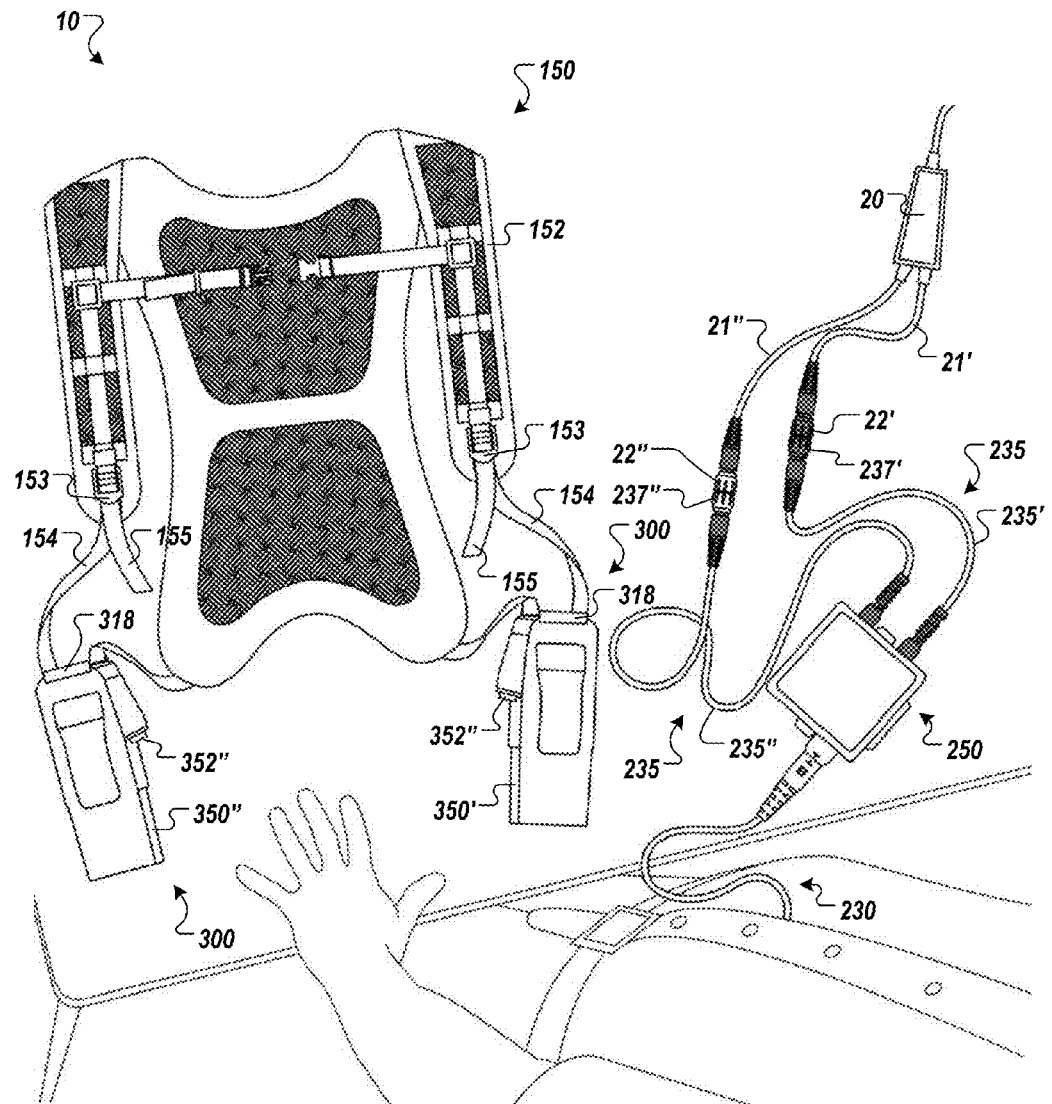
FIG. 11 is a top view of the medical device accessory carrier of FIG. 8A positioned on a table, in accordance with some embodiments.

The battery assembly 300 can be coupled to the holster vest 150, such that the battery assembly 300 hangs from one of the shoulder strap assemblies 152, using the adjusting strap 154. For example, FIG. 9 depicts a perspective view of a battery assembly coupled to a portion of the medical device carrier of FIG. 8A. The adjusting strap 154, connected to the back portion of the shoulder strap assembly 152, can be fed, from back to front, through the interior channel created by a strap loop 318 included in the top portion of the battery pouch 310 and through a buckle 153 included in the front of the shoulder strap assembly 152. When in this configuration, the weight of the battery assembly 300 can be substantially supported by the shoulder strap assembly 152. Furthermore, by adjusting the length of the free end 155 of the adjusting strap 154, the height of the battery assembly relative to the shoulder strap 152 (and therefore the person wearing the holster vest 150) can be adjusted. As the length of the free end 155 is shortened, the battery assembly 300 can hang lower. While the shoulder strap assembly 152, the adjustable strap 154, and the battery assembly 300 shown depict those found on the right side of the holster vest 150, the left side can be assembled and adjusted in a similar manner. While FIG. 11 represents one embodiment of the shoulder strap assembly 152 of the holster vest 150 that is made of one single piece of material, it should be appreciated that such holster vest 150 can be made of different configurations such as one or more strap assemblies with the intent of securing the battery assembly 300 as illustrated and providing a means for adjustability the position of the battery assembly 300 relative to the body of the user. Furthermore, the shoulder strap assembly 152 and the holster vest 150 can be made of a variety of material in different configurations for minimizing weight and maximizing comfort of the user. For example, nylon or other synthetic material can be used in a mesh configuration to minimize weight and to minimize bulkiness of the holster vest 150 or strap assembly 152 when worn underneath another garment such as a suit or a coat.

On the reverse side of the battery assembly 300, not shown in the figures, there can be a securing strap similar to the pocket 122 in FIG. 3A of the modular belt. This securing strap acts similar to a belt loop for securing the battery assembly 300 to the waist strap 162 or 164. In one embodiment, this securing strap can be rectangular in shape, mirroring the shape of the battery assembly 300, with a top end of the securing strap sewn onto the battery assembly 300 and a bottom end secured by Velcro. A user can either pass a belt or the waist strap 162 or 164 of the assembly between the securing strap and the battery assembly, or detach the Velcro end of the securing strap and slip the securing strap between a user's body and either a belt or the waist strap 162 or 164. The combination of anchoring the battery assembly to the shoulder strap 152 allows the weight of the battery assemblies to be distributed over the waist and the shoulder, and allows for adjusting the battery assemblies to a number of different positions for the most comfort.

Figure 10A:
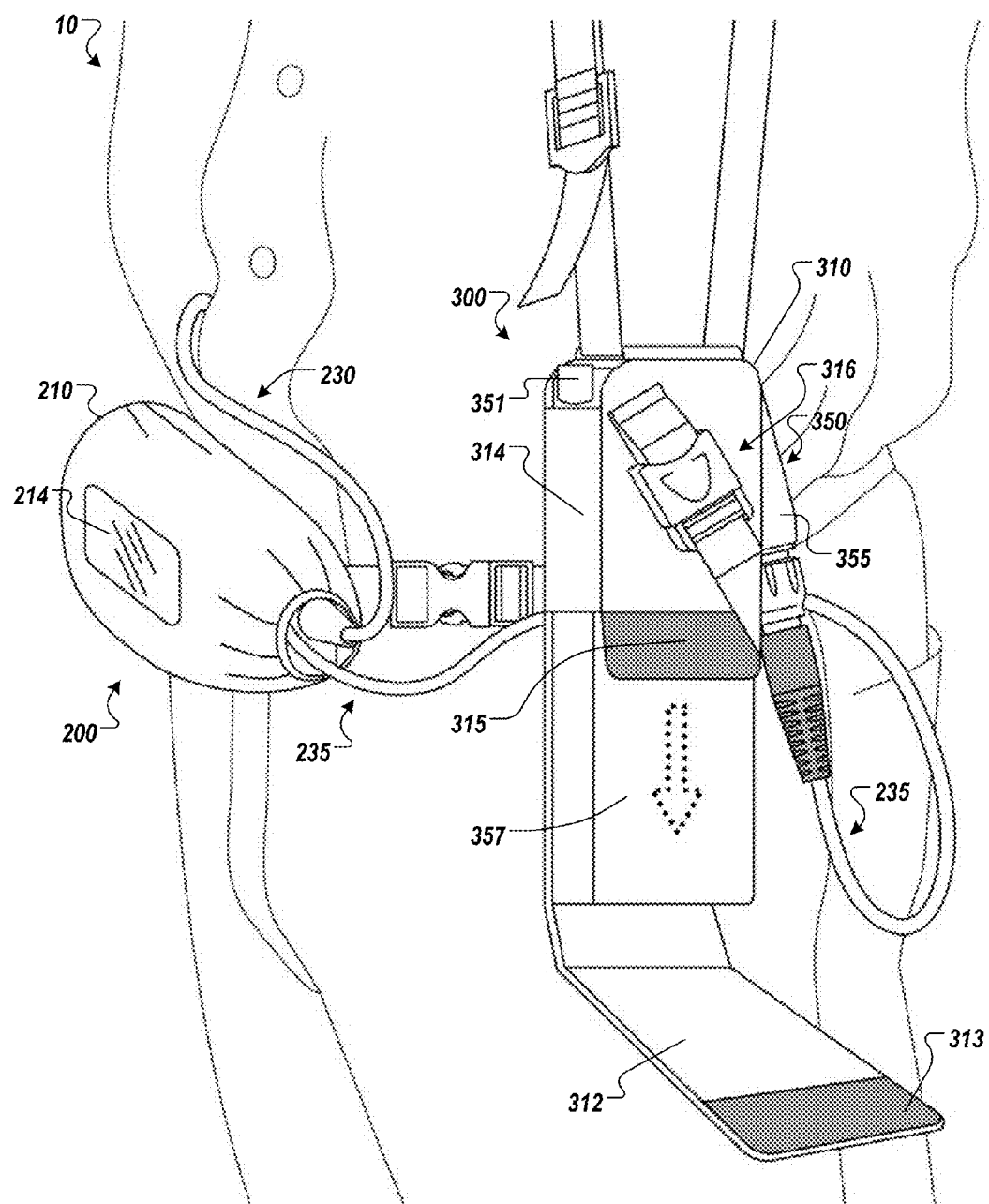
FIGS. 10A-B are side views of an embodiment of a battery assembly in an open configuration, in accordance with some embodiments.
Figure 10B:
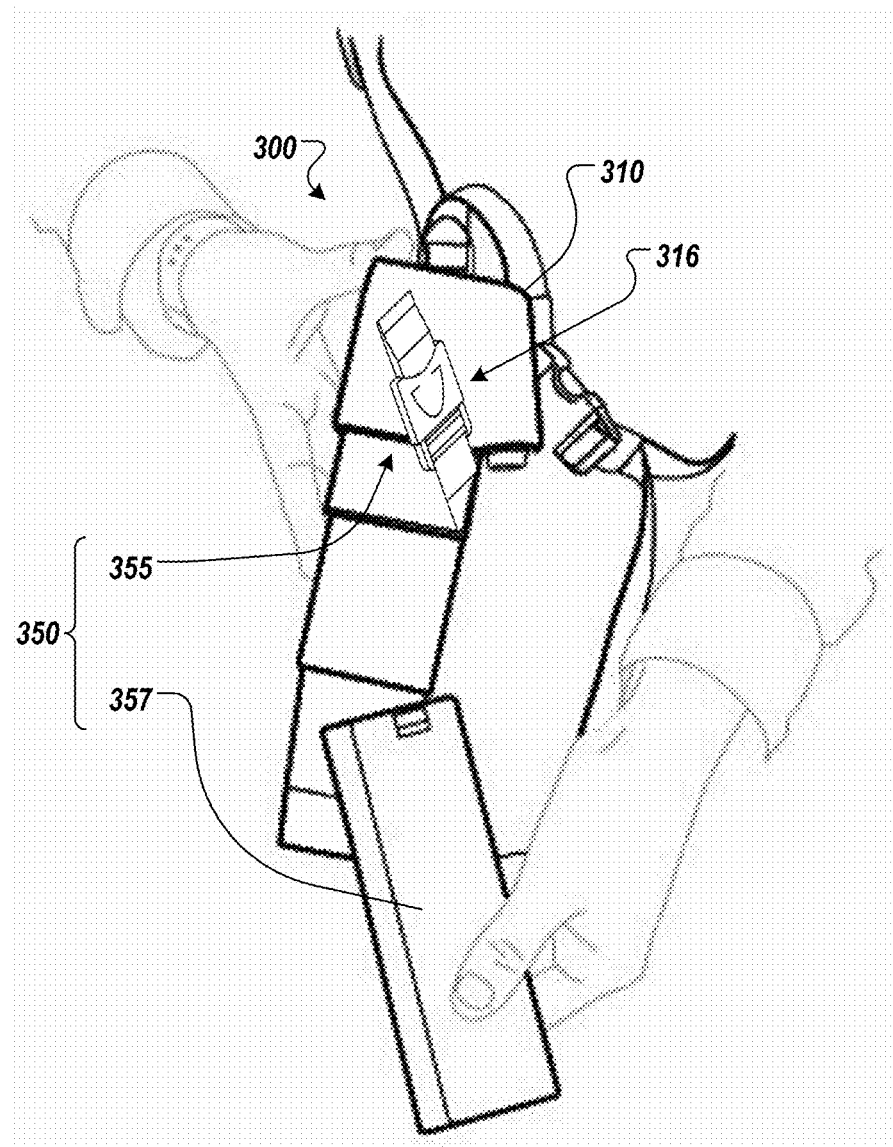

The carrier system 10 can include features that allow at least a portion of the battery 350 to be removed and replaced while a user is wearing the carrier system 10. For example, FIGS. 10A-B are side views of an embodiment of a battery assembly in an open configuration. The battery 350 can include a connector body 355 and a replaceable battery cell 357. To replace the battery cell 357, the battery pouch 310 can be transitioned from a closed configuration (depicted in FIGS. 1-2) to an open configuration where a portion of the battery 350 can be removed from the battery pouch 310. In a method similar to that described in connection with FIG. 5, application of a gentle outward force to the lower flap 312 substantially at the securing portion 313 can cause the securing portion 313 to separate from the underlying portion 315, thus transitioning the lower flap 312 to the open configuration shown in FIG. 10A. In some embodiments, a release button 351 can be pressed to uncouple the replaceable battery cell 357 from the connector body 355, allowing the replaceable battery cell 357 to slide downward and out of the battery pouch 310. A different battery cell 357 can be installed in the battery pouch 310 by reversing the removal steps. For example, a fully recharged battery cell 357 can be inserted into the battery pouch 310 until the battery cell 357 automatically engages the connector body 355 with an audible sound (such as a click) indicating the engagement mechanism (not shown) of the connector body 355 has engaged a portion of the battery cell 357 such that the engagement mechanism causes the replaceable battery cell 357 to be coupled to the connector body 355. The lower flap can be closed, causing the portions 313 and 315 to unite. At the discretion of the user, the battery assembly 300 can be uncoupled from the vest 150 (shown in FIG. 8A) prior to removal and replacement of the battery 350 (described in connection with FIG. 5) or the replaceable battery cell 357.

A user with an implanted medical device may have his movement limited by the accessories associated with the medical device. The user may employ the medical device accessory carrier system 10, including batteries 350' and 350" to achieve freedom of movement not obtainable without it. Briefly, in use, the user can place the holster vest 150 on a substantially flat surface, as shown in FIG. 11. FIG. 11 is a top view of the medical device accessory carrier of FIG. 8A positioned on a table. The user can couple the battery pouch 310 to the vest 150 and adjust the position of the battery pouch by threading an adjustment strap 154 through the strap loop 318, through the buckle 153, and adjusting the length of the free end 155 as described in connection with FIG. 9. The user can insert a second battery pouch 310 in a manner similar to the first. With the battery pouches 310 coupled to the modular belt, as shown in FIG. 11, the user can insert and secure one battery (e.g., the battery 350', the battery 350", and the like) into each of the pouches 310 as described in connection with FIGS. 5, 10A, and 10B.

Due at least in part to the presence of the two power leads 235, the controller device 250 can be transferred from a fixed power supply, such as the power supply 20, to a portable power supply (e.g., batteries) without interrupting the power supply to the controller device 250 or the medical device that is electrically connected to the controller device via the electrical lead 230. In use, the user can uncouple one of the electrical leads 235 (e.g., the electrical lead 235') from the power supply lead 21' at the connectors 237' and 22'. The connector 237' can then be coupled to the connector 352' on the battery 350'. While the electrical lead 235' is uncoupled from both the power supply 20 and the battery 350', power can still be received by the controller device 350 through the other electrical lead 235 (e.g., the electrical lead 235"). Once the lead 235' is reconnected to a power source (e.g., the battery 350'), the connector 237" can be uncoupled from connector 22" of power supply lead 21" and coupled to the connector 352" of the battery 350". When each of the electrical leads 235 is connected to a battery (e.g., the batteries 350' and 350"), the user can don the holster vest 150 to achieve a greater freedom of mobility than when he was connected to the non-portable power source 20.

The user can place the controller device 250 inside the controller pouch 210 as described in FIG. 4. When inside the controller pouch 210, the user can see the display 255 (FIG. 4) of the controller device 250 and can operate the input of the controller device 250. Using the clips 252 on the back of the controller device 250, the user can secure the controller assembly 200 (including the controller device 200, the pouch 210, and the like) to the waist-strap 160 and wear the strap 160 around his waist as depicted in FIG. 9. Similarly, the battery assembly 300 can also be secured to the waist strap assembly 160. The user can couple the controller device 250 to the strap assembly 160 without the use of the controller pouch 210.

Shower Bag

Figure 12:
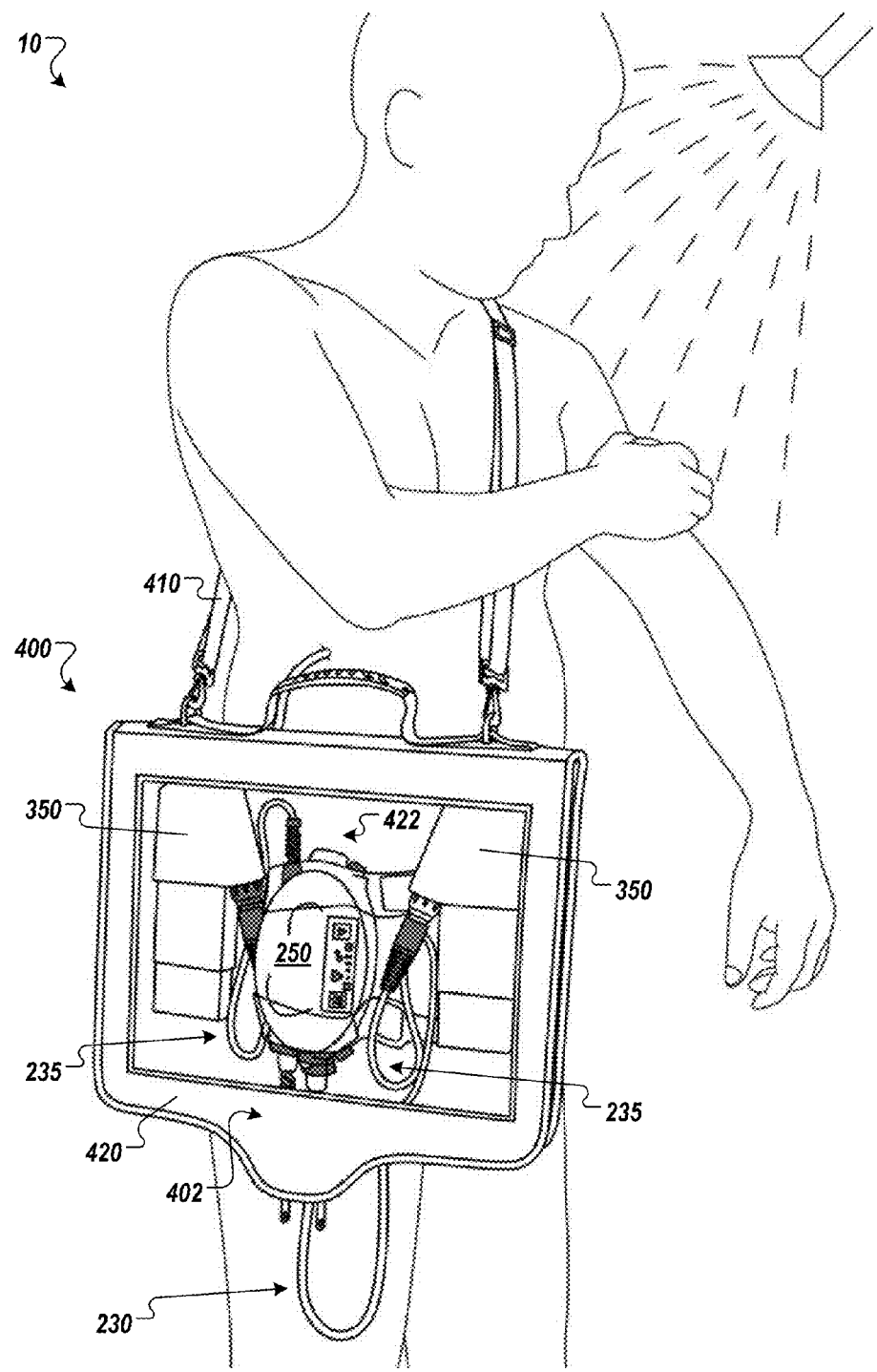
FIG. 12 is a perspective view of a water resistant medical device accessory carrier worn by a user, in accordance with some embodiments.

The medical device accessory carrier system 10 can be configured to be water resistant or water proof, for example, when used in the shower. For example, FIG. 12 is a perspective view of a water resistant or water proof medical device accessory carrier worn by a user. The carrier system 10 of FIG. 12 includes a water resistant or water proof case assembly 400. The water resistant or water proof case assembly 400 can include a shoulder strap 410 that can be worn around the shoulder of the user and can support the case assembly 400. The shoulder strap 410 can also be draped over a hook such that the weight of the case assembly 400 and any VAD accessories contained within (such as the batteries 350, controller device 250, and the like) are supported by the hook, thus increasing the mobility of the user. In this way, users of the carrier system 10 can have increased mobility in the shower while still being connected to the accessories used for the normal operation of an implanted VAD.

The case assembly 400 can securely hold at least two batteries 350 and the controller device 250 in a substantially planar arrangement thus minimizing the height of the case assembly 400. When in this planar arrangement, a user can access individual items contained within the case assembly 400 without disturbing the other contents of the case assembly 400. For example, when the case assembly 400 is positioned on a surface such that the top face 402 (see FIG. 12) of the case assembly 400 is facing up, a top flap 420 of the case assembly 400 can be opened such that the case assembly 400 is transitioned from the closed configuration shown in FIG. 12 to the open configuration shown in FIG. 13 and the contents of the case assembly 400 become accessible to the user. If the user desires to remove one of the batteries 350 (e.g., to replace the battery 350 with a fully charged battery 350) the user can do so without disturbing the other battery 350 positioned in the case assembly 400, the controller device 250, or the associated power and electrical leads 230 and 235. As such, removal and replacement of contents of the case assembly 400 is facilitated.

The top flap 420 can include features such that the operation of the implanted medical device can be monitored and controlled without having to remove the controller device 250 from the case assembly 400. For example, the top flap 420 can include a see-through portion 422 that allows the user to monitor the display 255 of the controller device 250. In another example, the see-through portion 422 can include a flexible material such that the input of the controller device 250 (e.g., buttons, a touch-sensitive screen, a membrane keyboard, and the like) can be operated by the user without requiring that the controller device 250 be removed from the case assembly 400.

At least a portion of the case assembly 400 can be made with a STAMOID material that is common to the marine industry for boat covers and shade tops. This material may also be used as cover material for awnings and shade canopies. In some embodiments, a clear urethane window is ultrasonically welded into the case assembly 400 to form see-through portion 422. The perimeter of the case assembly 400 and the see-through portion 422 may have a layer of sealing tape sandwiched into the assembly to assure excellent sealing from water ingress during a shower or other water exposure. Additionally, binding tape may be used that finishes off the case assembly 400. The sealing tape may be heated to seal the stitching holes to keep the inside of the case assembly 400. In other embodiments, other waterproof/resistant materials may be used instead of STAMOID such as vinyl-coated polyester or a woven acrylic.

The case assembly 400 can include features that allow the electrical lead 230 to pass from the inside of the case assembly 400 to the outside of the case assembly 400. An example of this can be seen in FIG. 13, which is a top view of the water resistant medical device accessory carrier of FIG. 12 in an open configuration laid flat on one side of the medical device accessory carrier. The case assembly 400 can include a zipper assembly 405 including two zippers 406. The two zippers 406 can be closed against two corresponding stops 407, thus leaving a channel 408 through which the electrical lead 230 can pass. Due in part to the fact that the channel 408 is located in the lower edge of the case assembly 400 (when the case is oriented vertically as depicted in FIG. 12), water is discouraged from entering the case assembly 400. In other embodiments, the orientation of the controller assembly 250 when inserted in the case assembly 400 can be configured so that the electrical lead 230 exits the side of the case assembly 400 rather than at the bottom. Additionally, zipper stops may be integrated in the case assembly 400 so that the zipper is stopped before reaching and possibly damaging the electrical lead 230.

Consolidated Bag

Figure 14:
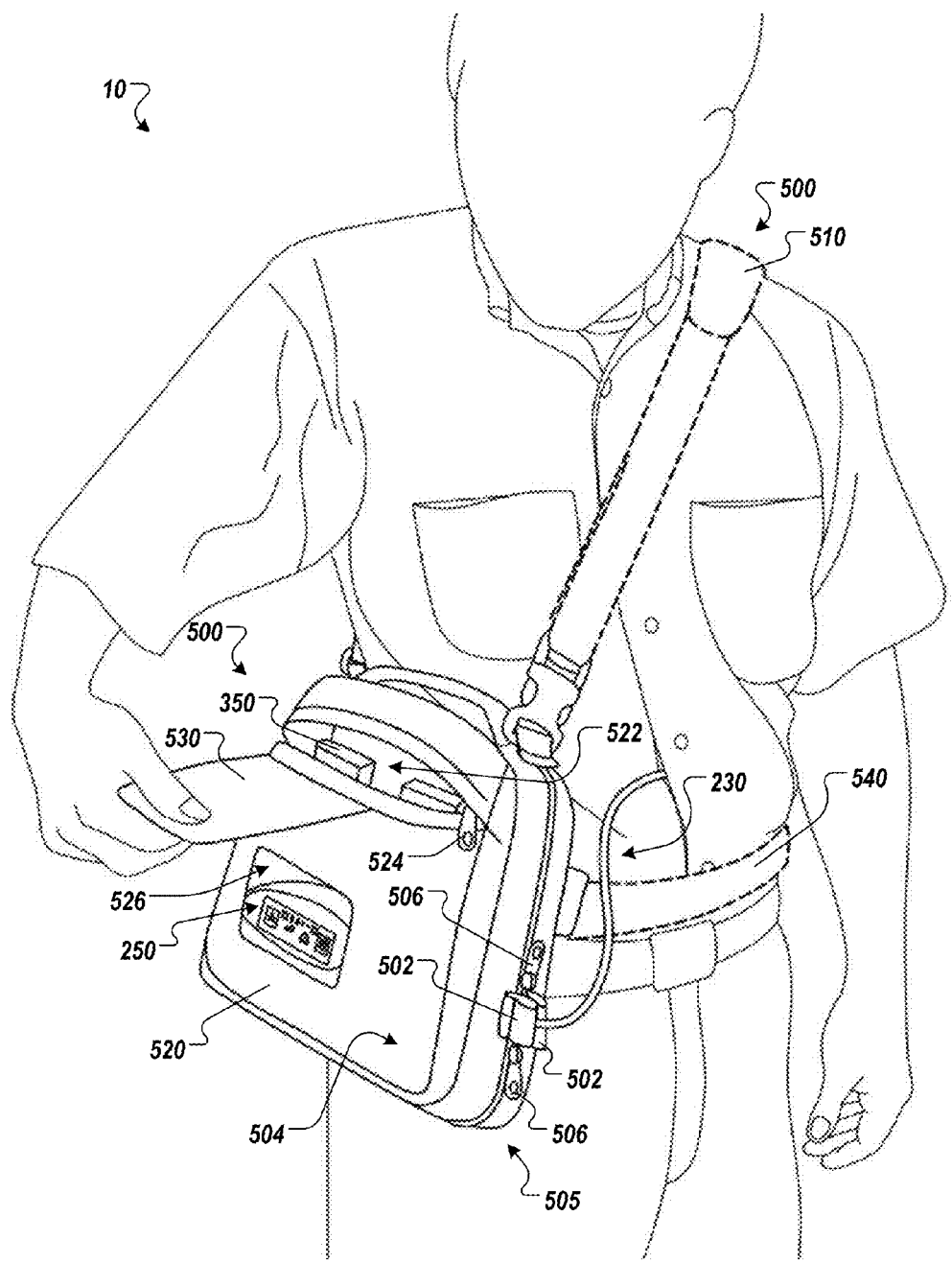
FIG. 14 is a perspective view of another embodiment of a medical device accessory carrier worn by a user, in accordance with some embodiments.
Figure 15:
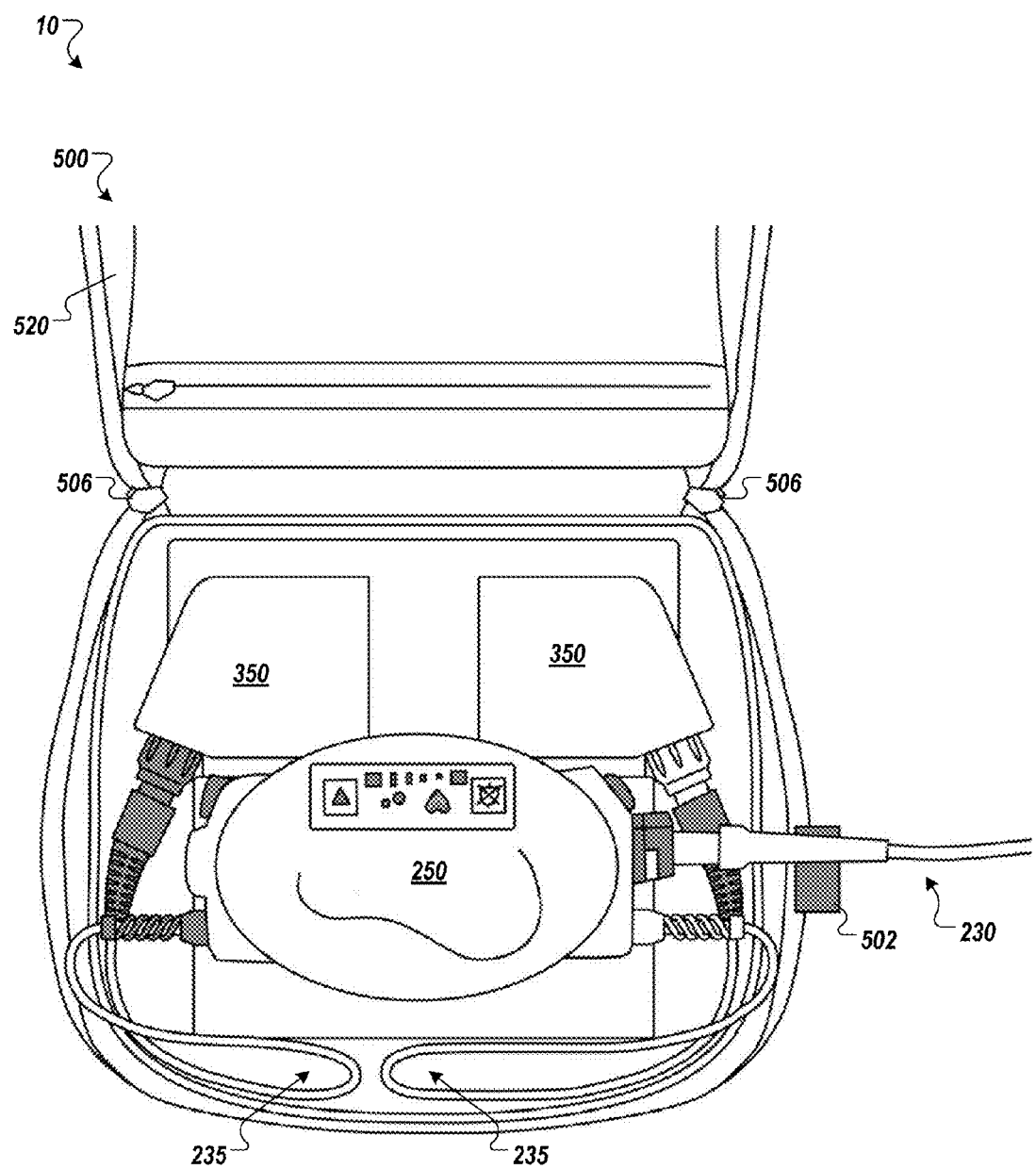
FIG. 15 is a top view of the medical device accessory carrier of FIG. 14, in an open configuration, in accordance with some embodiments.

The medical device accessory carrier system 10 can be configured to be carried over the shoulder of the patient, for example, like a laptop computer. For example, FIG. 14 is a perspective view of another embodiment of a medical device accessory carrier worn by a user. FIG. 15 depicts a top view of the medical device accessory carrier of FIG. 14, in an open configuration. The carrier system 10 of FIG. 14 includes a laptop-style case assembly 500. The case assembly 500 can include a shoulder strap 510, for example, that can be worn around the shoulder of the user and can support the case assembly 500. The shoulder strap 510 can also be draped over a hook such that the weight of the case assembly 500 and any VAD accessories contained within (such as the batteries 350, controller device 250, and the like) are supported by the hook, thus increasing the mobility of the user. In this way, users of the carrier system 10 can have increased mobility while still being connected to the accessories used for the normal operation of an implanted VAD. The case assembly 540 can a waist belt 540, which can be optionally worn by the user. The waist belt 540 can wrap around a majority of the user's waist and coupled to a portion of the case assembly 500 (e.g., a back side), for example, using snap connectors. The waist belt 540 can be optionally worn by the user to increase the security and the stability of the case assembly 500. For example, the waist belt 540 can maintain the case assembly 500 against the user's side during activities that would otherwise cause the case assembly to move uncontrollably away from the user. During activities when the user wants additional mobility, the optional waist strap 540 can be uncoupled from case assembly 500. The batteries 350 can be accessed while inside the case assembly 500, without having to transition the case assembly 500 to the fully open configuration shown in FIG. 15. For example, the case assembly 500 can include a top flap 520 that includes an orifice 522 that can be closed using a zipper assembly 524. When the zipper assembly is positioned as in FIG. 14, the batteries 350 located inside the case assembly 500 can be accessed by the user. In this way, a user can remove one or more of the batteries 350, disconnect them from the other medical device accessories, and replace them, without having to fully open the case assembly 500.

Figure 13:
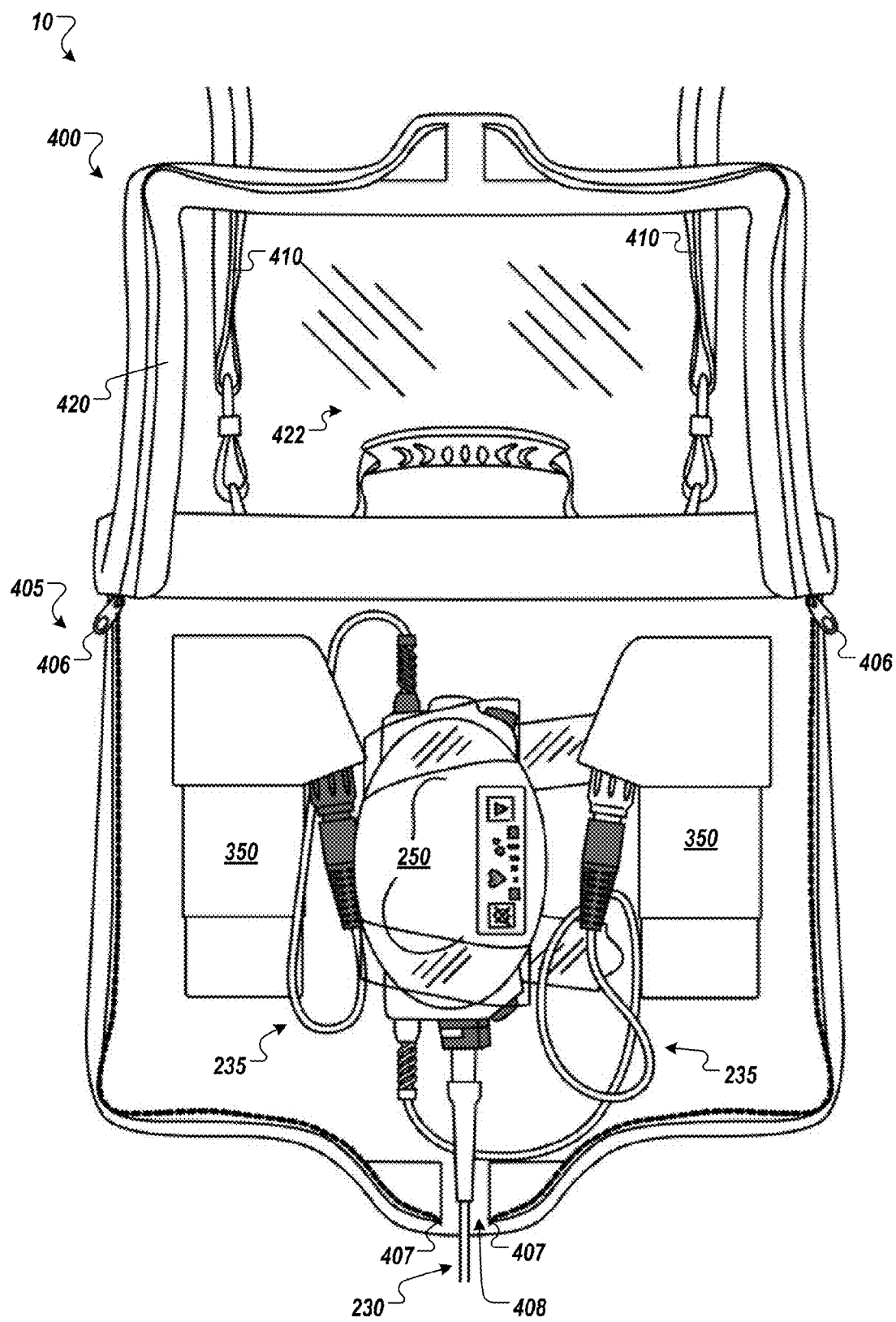
FIG. 13 is a top view of the water resistant medical device accessory carrier of FIG. 12 in an open configuration, in accordance with some embodiments.

Similar to shower bag embodiment of FIGS. 12 and 13, discussed above, the case assembly 500 of FIGS. 14 and 15 can include the top flap 520 with features such that the operation of the implanted medical device can be monitored and controlled by the controller device 250 without having to remove the controller device 250 from the case assembly 500. For example, the top flap 520 can include a see-through portion 526 that allows the user to monitor the display of the controller device 250. In another example, the see-through portion 526 can include a flexible material such that the input of the controller device 250 (e.g., buttons, a touch-sensitive screen, a membrane keyboard, and the like) can be operated by the user without requiring that the controller device 250 be removed from the case assembly 500. In some embodiments, it may be advantageous for the user to normally obscure the contents of the case assembly 500. For example, the user may not want passers-by to be aware that he is using an implantable medical device. It may also be advantageous, while out in public, to protect the controller device 250 from accidental activation, such as would occur if a passer-by accidentally made contact with the case assembly 500 in the approximate location of an input of the controller device 250. As such, the case assembly 500 can include a semi-rigid flap 530 configured to conceal the see-through portion 526 during normal use. With the flap 530 hanging down over the see-through portion 526, the contents of the case assembly 500 (e.g., the controller device 250) can be concealed from view. In embodiments where the flap 530 is somewhat rigid, inadvertent triggering of the controller device 250 can be reduced. To visualize the controller device 250, the user can lift up on the flap 530 as depicted in FIG. 14.

The case assembly 500 can include features that allow the electrical lead 230 to pass from the inside of the case assembly 500 to the outside of the case assembly 500. For example, the case assembly 500 can include a zipper assembly 505 including two zippers 506. When in the configuration depicted in FIG. 14, the two zippers 506 can be closed against either side of two corresponding protective flaps 502. Features such as the protective flaps 502, stops in the zipper assembly 505, and the like, can allow the user to close and secure the case assembly 500, maintain an opening through which the electrical lead 230 can pass, and protect the electrical lead 230 from damage due to the zippers 506.

The case assembly 500 as shown in FIGS. 14 and 15 can securely hold two batteries 350 and one controller device 250 in a substantially planar arrangement thus minimizing the height of the case assembly 500. When in a planar arrangement, a user can access individual items contained within the case assembly 500 without disturbing the other contents of the case assembly 500. For example, when the case assembly 500 is positioned on a surface such that the top face 504 (see FIG. 14) of the case assembly 500 is facing up, the top flap 520 can be opened such that the case assembly 500 is transitioned from the closed configuration shown in FIG. 14 to the open configuration shown in FIG. 15 and the contents of the case assembly 500 become accessible to the user. If the user desires to remove one of the batteries 350 (e.g., to replace the battery 350 with a fully charged battery 350) the user may do so without disturbing the other battery 350, the controller device 250, or the associated power and electrical leads 230 and 235. As such, removal and replacement of contents of the case assembly 500 is facilitated. In other embodiments, the case assembly 500 can hold additional batteries.

Alternative Embodiments

In some embodiments, the medical device accessory carrier system 10 can include configurations not described above for containing accessories associated with an implanted medical device, such as a ventricular assist device. For example, the system 10 can include a battery assembly (not shown) that can contain two batteries 350. In another example, the modular system 10 can include a case assembly (not shown) that can contain a controller device 250 and two batteries 350 and can be coupled to the modular belt 100. The modular belt assembly can include optional straps, such as a shoulder strap, that can be draped over the shoulder of a user and can support at least a portion of the weight of the system 10 and associated accessories. In some embodiments, one or more of the controller assembly 200 and the battery assemblies 300 can be coupled to a shoulder strap or the neck strap 110. In some embodiments, the modular belt 100, the holster vest 150, the neck strap 110, a shoulder strap, and the like can include quick connected features allowing the user to easily remove and reconnect components of the system 10.

In alternative embodiments, the medical device accessory carrier system 10 can be used with implanted medical devices that differ from the ventricle assist devices specifically described herein. The medical device accessory carrier system 10 can be used with an implanted blood pump that includes no percutaneous leads. For example, an implanted pump can use a wireless connection to an external controller and can receive power through transcutaneous power transmission. To maintain substantially uninterrupted transfer of power from external to internal coils, the external coils may be maintained near the user skin. To maximize the efficiency of power transmission, the external coil may be maintained in a specific location adjacent to the user's skin in close proximity to the internal coils by the accessory carrier system 10. The medical device accessory carrier system 10 can be used with an implanted blood pump that includes additional percutaneous leads. For example, the medical device accessory carrier system 10 can be used with an implanted pneumatic blood pump that includes both electrical and pneumatic percutaneous leads. Additionally, the medical device accessory carrier system 10 can be used with other implanted pumps and devices, such as insulin pumps, pumps delivering therapeutic drugs, pumps delivering main management drugs, stimulators, and the like.

A number of embodiments have been described. Nevertheless, it will be understood that various modifications may be made without departing from the spirit and scope of this disclosure. Accordingly, other embodiments are within the scope of the following claims.

What is claimed is:

1. A carrier system for carrying medical device accessories comprising:
    a garment to be worn about a user's torso including left and right shoulder assemblies interconnected by a back portion, the shoulder assemblies configured to drape over respective left and right shoulders of a user with the back portion against a user's back;
    left and right straps; and
    first and second battery pouches each configured to enclose at least a portion of a battery, the battery pouches configured to hang from the straps for positioning along a side of the user's torso, each strap with hanging pouch extending in use between a respective left or right shoulder assembly at the front of the user and the back portion around a respective side of the user,
    wherein each strap is configured to have its length adjusted by the user to adjust the position at which the pouch hangs;
    a waist-strap coupled with the left and right straps and configured to be worn about a user's waist, the waist-strap adapted to allow for attachment of a medical device controller that is electrically connected to a medical device;
    a controller retainer coupled with the waist-strap, the controller retainer configured to receive the medical device controller, the controller retainer comprising:
        a backing plate coupled to a back portion of the controller retainer, the backing plate including an opening for cooperating with a clip of a medical device controller.

2. The carrier system of claim 1, wherein the carrier system further comprises:
    a generally u-shaped first clip rotatably attached to at least one of the first and second battery pouches and adapted to fit over at least a portion of the waist-strap, the first clip permitting the at least one of the first and second battery pouches to rotate relative to the garment.

3. A carrier system for carrying batteries of a medical device comprising:
    a garment to be worn about a torso, the garment comprising at least a first shoulder strap assembly adapted to drape over one shoulder of a user and extend generally vertically over a user's torso and back near a side of the user, the garment also comprising a waist-strap adapted to be worn about a user's waist, the waist-strap adapted to allow for attachment of a medical device controller that is electrically connected to a medical device;
    a first strap extending in use between a portion of the first shoulder strap assembly at the front of the user and another portion of the first shoulder strap assembly at the back of the user;
    a first battery pouch to enclose at least a portion of a first battery, the first battery pouch configured to attach to the first shoulder assembly by hanging from the first strap;
    a generally u-shaped first clip rotatably attached to the first battery pouch and adapted to fit over a portion of the waist-strap at the same time that the first battery pouch is attached to the first shoulder strap assembly, the first clip permitting the first battery pouch to rotate relative to the waist-strap; and
    a controller retainer coupled to the waist-strap, the controller retainer configured to receive the medical device controller, the controller retainer having a backing plate coupled to a back portion of the controller retainer, the backing plate including an opening configured to cooperate with one or more clips included on the medical device controller, the opening configured to receive the clip through the opening when the controller device is received within the controller retainer such that a portion of the clip protrudes out of the controller retainer.

4. The carrier system of claim 3, wherein the carrier system further comprises:
    a second shoulder strap assembly adapted to drape over a second shoulder of a user and extend generally vertically over a user's torso and back near a second side of the user;
    a second strap extending in use between a portion of the second shoulder strap assembly at the front of the user and another portion of the second shoulder strap assembly at the back of the user;
    a second battery pouch to enclose at least a portion of a second battery, the second battery pouch configured to attach to the second shoulder assembly by hanging from the second strap; and
    a generally u-shaped second clip rotatably attached to the second battery pouch and adapted to fit over a portion of the waist-strap, the second clip permitting the second battery pouch to rotate relative to the waist-strap.

5. The carrier system of claim 1, wherein the waist-strap further comprises an adjustable strap that is adapted to connect to the controller pouch via at least one snap-fit connection.

6. The carrier system of claim 1, wherein the waist-strap comprises a waist adjustment feature to adjust the length of the waist-strap.

7. The carrier system of claim 3, wherein the waist-strap comprises an adjustment feature configured to allow for an adjustment of the length of the waist-strap.

8. The carrier system of claim 1, wherein the battery pouches are configured to hang from the straps for positioning near a user's hips.

9. A carrier system for carrying medical device accessories, comprising:
a garment to be worn about a user's torso including left and right shoulder assemblies interconnected by a back portion, the shoulder assemblies configured to drape over respective left and right shoulders of a user with the back portion against a user's back;
left and right straps; and
first and second battery pouches each configured to enclose at least a portion of a battery, the battery pouches configured to hang from the straps for positioning along a side of the user's torso, each strap with hanging pouch extending in use generally vertically from a respective left or right shoulder assembly at the front of the user around a side of the user to the back portion when the user is standing;
wherein each strap is configured to have its length adjusted by the user to adjust the position at which the pouch hangs;
a waist-strap coupled with the left and right straps and adapted to be worn about a user's waist, the waist-strap adapted to allow for attachment of a medical device controller that is electrically connected to a medical device;
a controller pouch coupled with the waist strap, the controller pouch configured to enclose at least a portion of the medical device controller, the controller pouch having a backing plate coupled to a back portion of the controller pouch, the backing plate including an opening configured to cooperate with one or more clips included on the medical device controller, the opening configured to receive the clip through the opening when the controller device is placed within the controller pouch such that a portion of the clip protrudes out of the controller pouch.

10. The carrier system of claim 9, wherein the waist-strap is adapted to allow for attachment of a medical device controller that is electrically connected to the medical device while at the same time allowing for attachment of at least one of the first and second battery pouches.

11. The carrier system of claim 9, wherein the waist-strap further comprises an adjustable strap that is adapted to connect to the controller pouch via at least one snap-fit connection.

12. The carrier system of claim 1, wherein each strap with hanging pouch extends in use between a lower terminal end of the respective left or right shoulder assembly at the front of the user and the back portion around the respective side of the user.

13. The carrier system of claim 1, wherein the opening is configured to receive the clip through the opening when the controller device is placed within the controller retainer such that a portion of the clip protrudes out of the controller retainer.

14. The carrier system of claim 1, wherein the controller retainer comprises a controller pouch for enclosing the controller device, and wherein the controller pouch includes:
left and right openings configured to receive one or more power cords from batteries disposed in the first and second battery pouches and one or more cords from the medical device; and
wherein the controller pouch is configured to receive and enclose the medical device controller while the medical device controller remains coupled with the one or more power cords from the batteries disposed in the first and second battery pouches and the one or more cords from the medical device.

15. The carrier system of claim 14, wherein the controller pouch further comprises a transparent window so as to allow a user to monitor the medical device controller disposed within the controller pouch without having to remove the medical device controller from the controller pouch, the transparent window comprising a flexible material such that the user may operate the medical device controller without having to remove the medical device controller from the pouch.

16. The carrier system of claim 14, wherein the controller pouch is configured to receive the medical device controller through a second opening between an upper flap and a lower flap, and wherein a user closes the controller pouch and secures a medical device controller by pulling the lower flap along the front face of the received medical device controller and by pulling the upper flap toward the lower flap, overlapping a portion of the lower flap with the upper flap; and securing the upper flap with the lower flap such that the overlap is maintained.

17. The carrier system of claim 14, wherein the controller pouch is manufactured from a water resistant material.

18. The carrier system of claim 1, wherein the battery pouches include a first opening configured to receive a battery and a second opening separate from the first opening, the second opening configured to provide power cord access between a stored battery and the medical device controller.

19. The carrier system of claim 3, wherein the controller retainer comprises a controller pouch for enclosing the controller device, and wherein the controller pouch includes:
left and right openings configured to receive one or more power cords from batteries disposed in the first and second battery pouches and one or more cords from the medical device; and
wherein the controller pouch is configured to receive and enclose the medical device controller while the medical device controller remains coupled with the one or more power cords from the batteries disposed in the first and second battery pouches and the one or more cords from the medical device.

20. The carrier system of claim 19, wherein the controller pouch further comprises a transparent window so as to allow a user to monitor the medical device controller disposed within the controller pouch without having to remove the medical device controller from the controller pouch, the transparent window comprising a flexible material such that the user may operate the medical device controller without having to remove the medical device controller from the pouch.

21. The carrier system of claim 19, wherein the controller pouch is configured to receive the medical device controller through a second opening between an upper flap and a lower flap, and wherein a user closes the controller pouch and secures a medical device controller by pulling the lower flap along the front face of the received medical device controller and by pulling the upper flap toward the lower flap, overlapping a portion of the lower flap with the upper flap; and securing the upper flap with the lower flap such that the overlap is maintained.

22. The carrier system of claim 3, wherein the controller pouch is manufactured from a water resistant material.

23. The carrier system of claim 3, wherein the battery pouches include a first opening configured to receive a battery and a second opening separate from the first opening, the second opening configured to provide power cord access between a stored battery and the medical device controller.

* * * * *